US008558058B2

(12) United States Patent
Hood et al.

(10) Patent No.: US 8,558,058 B2
(45) Date of Patent: Oct. 15, 2013

(54) MONOCOTYLEDONOUS SEED EXPRESSING EXO-1,4B-GLUCANASE

(75) Inventors: Elizabeth Hood, Jonesboro, AR (US); John Howard, College Station, TX (US)

(73) Assignee: Applied Biotechnology Institute, San Luis Obispo, CA (US)

( * ) Notice: Subject to any disclaimer, the term of this patent is extended or adjusted under 35 U.S.C. 154(b) by 1749 days.

(21) Appl. No.: 11/219,180

(22) Filed: Sep. 2, 2005

(65) Prior Publication Data

US 2006/0026715 A1 Feb. 2, 2006

Related U.S. Application Data

(63) Continuation-in-part of application No. 10/310,292, filed on Dec. 6, 2002, now abandoned.

(60) Provisional application No. 60/340,035, filed on Dec. 6, 2001, provisional application No. 60/607,098, filed on Sep. 3, 2004.

(51) Int. Cl.
*C12N 15/82* (2006.01)
*A01H 5/00* (2006.01)

(52) U.S. Cl.
USPC ........... 800/287; 800/278; 800/284; 800/288; 800/295; 800/298; 800/320; 800/320.1

(58) Field of Classification Search
None
See application file for complete search history.

(56) References Cited

U.S. PATENT DOCUMENTS

| | | | |
|---|---|---|---|
| 4,287,304 A | 9/1981 | Muller et al. | 435/162 |
| 4,302,543 A | 11/1981 | Benyaev et al. | 435/161 |
| 4,330,625 A | 5/1982 | Miller et al. | 435/161 |
| 4,347,321 A | 8/1982 | Lionelle et al. | 435/161 |
| 4,407,955 A | 10/1983 | Muller et al. | 435/161 |
| 4,415,659 A | 11/1983 | Ronkainen et al. | 435/161 |
| 4,416,989 A | 11/1983 | Kretz | 435/93 |
| 4,425,433 A | 1/1984 | Neves | 435/163 |
| 4,448,881 A | 5/1984 | Muller et al. | 435/162 |
| 4,617,270 A | 10/1986 | Anderson et al. | 435/161 |
| 4,810,647 A | 3/1989 | Monceaux et al. | 435/106 |
| 4,952,503 A | 8/1990 | Granstedt | 435/161 |
| 5,100,791 A | 3/1992 | Spindler et al. | 435/163 |
| 5,231,017 A | 7/1993 | Lantero et al. | 435/161 |
| 5,543,576 A | 8/1996 | Van Ooijen et al. | 800/250 |
| 5,545,543 A | 8/1996 | Zinnamosca et al. | 435/162 |
| 5,677,154 A | 10/1997 | Van Draanen et al. | 435/163 |
| 5,932,456 A | 8/1999 | Van Draanen et al. | 435/144 |
| 5,981,237 A | 11/1999 | Meagher et al. | 435/99 |
| 5,981,835 A | 11/1999 | Austin-Phillips et al. | 800/278 |
| 6,013,860 A * | 1/2000 | Himmel et al. | 800/278 |
| 6,818,803 B1 | 11/2004 | Autin-Phillips et al. | |
| 7,102,057 B2 | 9/2006 | Lanahan et al. | |
| 7,361,806 B2 | 4/2008 | Lebel et al. | |
| 2003/0074700 A1 * | 4/2003 | Huang et al. | 800/288 |
| 2003/0109011 A1 | 6/2003 | Hood et al. | |
| 2008/0022425 A1 | 1/2008 | Lebel et al. | |
| 2008/0078005 A1 | 3/2008 | Lebel et al. | |

FOREIGN PATENT DOCUMENTS

| | | | | |
|---|---|---|---|---|
| WO | WO 9725468 | 7/1997 | | D06M 16/00 |
| WO | WO 9839461 | 11/1998 | | C12N 15/82 |
| WO | WO 99/16890 | * 4/1999 | | C12N 15/82 |
| WO | WO 9916890 | 4/1999 | | C12N 15/82 |

OTHER PUBLICATIONS

Horvath et al. The production of recombinant proteins in transgenic barley grains. (2000) PNAS, vol. 97, pp. 1914-1919.*
Dai et al. Over-expression of cellulases in transgenic tobacco whole plants. (1998) Poster: ASPP Annual Meeting, vol. 1998, p. 85.*
Dai et al. Expression of *Trichoderma reesei* exo-cellobiohydrolase I in transgenic tobacco leaves and calli. (1999) Appl. Biochem. and Biotech.; vol. 77-79, pp. 689-699.*
Matzke et al. Deletion analysis of a zein gene promoter in transgenic tobacco plants. (1990) PMB; vol. 14, pp. 323-332.*
Dai et al. Expression of *Trichoderma reesei* Exo-cellobiohydrolase I in trnasgenic tobacco leaves and calli. (1999) In: Applied Biochemistry and Biotechnology; vol. pp. 77-79.*
Whitelam, G. C. The production of recombinant proteins in plants. (1995) J. Sci. Food Agric.; vol. 68; pp. 1-9.*
Napier et al. Trafficking and stability of heterologous proteins in transgenic plants. (1998) In: Methods in Biotechnology; vol. 3: Chapter 15, pp. 189-202.*
Rishi et al . Molecular Farming in plants: a current perspective. (2001) J. Plant Biochem. & Biotech.; vol. 10, pp. 1-12.*
Law et al. Biochemical limitations to high-level expression of humanized monoclonal antibodies in transgenic maize seed endosperm. (2006) Biochimica et Biophysica Acta; vol. 1760; pp. 1434-1444.*
Verwoerd, TC, et al. Stable accumulation of *Aspergillus niger* phytase in transgenic tobacco leaves. Plant Physiol 109:1199-1205(1995).
Hood, EE, et al. Commercial production of avidin from transgenic maize: Characterization of transformat, production, processing, extraction and purification. Molecular Breeding 3:291-306 (1997).
Ziegler, MT, et al. Accumulation of a thermostable endo-1, 4-β-D-glucanase in the apoplast of *Arabidopsis thaliana* leaves. Molecular Breeding 6:37-46 (2000).
Dai, Z at al. Improved plant-based production of E1 endoglucanase using potato: expressin optimization and tissue targeting. Moleculant Breeding 6:277-285 (2000.
Ziegelhoffer, T, et al. Expression of bacterial cellulose genes in transgenic alfalfa (*Medicago sativa* L.) potato (*Solanum tuberosum* L) and tobacco (*Nicotiana tabacum* L.)Molecular Breeding 4:309-318 (1999).
Jensen LG, et al. Transgenic barley expressing a protein-engineered, thermostable (1,3-1,4)-β-glucanase during germination. Proc. Natl. Acad. Sol. U.S.A. 93:3487-3491 (1996).

(Continued)

*Primary Examiner* — Cathy Kingdon Worley
(74) *Attorney, Agent, or Firm* — Patricia A. Sweeney

(57) ABSTRACT

Expression of recombinant polysaccharide degrading enzymes in plants is described. In one embodiment, expression of the enzyme is preferentially directed to the seed of the plant. Expression may also be preferentially targeted to specific locations within the plant cell. Expression of cellulases in corn is shown. The result is the capacity to produce polysaccharide degrading enzymes in plants at commercially acceptable levels in a reliable manner. Methods of using same in production of ethanol is also described, including use of the plant-produced enzymes in the ethanol production process.

24 Claims, 24 Drawing Sheets

(56) References Cited

OTHER PUBLICATIONS

Lacki, K, et al. stability of a Polyphenol oxidase from the white-rot-fungus Trametes versicolor in the presence of conola meal. Acta Biotechnol. 19 (1999) 2. 91-100.

Nieves et al. Quantitation of *Acidothermus cellulolyticus* E1 Enddoglucanase and *Thermomono ospora* fusca E3 Exoglucanase using Enzme-Linked Immunosorbent Assay (ELISA). Applied Biochemistry and Biotechnology vol. 51/52, 1995.

Tucker, et al. Ultra-Thermostable cellulases from *Acidothermus celluloyticus*: comparison of temperature optima with previously reported cellulases. Bio/Technology vol. 7 Aug. 1989.

Blum et al. Feruloyl Esterase of the *Clostridium thermocellum* cellulosome can be attributed to previously unknown domains of XynY and XynZ. Journal of Bacteriology, Mar. 20000, p. 1346-1351, vol. 182, No. 5.

Zhong et al. Commercial production of aprotihin in transgenic maize seeds. Molecular Breeding 5. 345-358, 1999.

Walsh et al. Biomass Feedback Avalibility in the United States: 1999 State Level Analysis http://bioenergy.ml.gov/resoucedata/index.html.

Hood, et al. Molecular farming of industrial protines from transgenic maize, Chemicals via Higher Plant Bioengerneering, edited by Shahidi et al. Kluwer Acidemi/Plenum Publishers, New York, 1999.

Baker, et al A New Thermostable Endoglucanase, *Acidothermus cellulolyticus* E1 Applied Biochemistry and Biotechnology. vol. 45-46, 1994.

Sreenath, et al. Enzymic sacharification of alfalfa fiber after liquid hot water pretreatment. Process Biochemistry 35 (1999) 33-34.

Lid, J-H, et al. Plant seed oil-bodies as an immobilization matrix for a recombinant zylanase from the rumen fungus *Neocallimastix patricarum*. Molecular Breeding 3: 463-470 (1997).

Sheehan, J: The road to biothanal: A statigec perspective of the U.S. Department of Energy's National Ethenol Program. Glycosyl Hydrolases for Biomass Conversion, pp. 2-25 (2001).

Maijala, P. Heterobasidion annosum and wood decay: Enzymology of cellulose, hemicelluose and lignin degradation, Dissertation, University of Helskinki, Mar. 31, 2000.

Corn Stover Harvesting Field Demonstation and Biomass Harvesting Colloquium, Record and Minutes of Program, Hamlan Iowa, Oct. 29, 2001.

Brown, R.C. et al, Harvest, Handlling, and Densification for Commercial Processing of Biomass Feedstock, U.S. DOE Aug. 1, 2000.

McAloon, A. et al. Determining the Cost of Producing Ethenol from Corn Starch and Lignocellulosic Feedstocks, Technical Report, NREL/TP-580-28893, Oct. 2000.

Wooley, R. et al. Lignocellulosic Biomass to Ethenol Proces Design and Economics Utilizing Co-Current Dilute Acid Prehydrolysis and Enzymatic Hyrdolysls Current and Futuristic Scenarios, Technical Report, NREL/TP-580-26157, Jul. 1999.

Aspegren et al. Molecular Breeding 1: 91-99 (1995).

Hooker et al. pp. 55-90 In: Glycosyl Hydrolases for Biomass Conversion, ACs Symposium Series, vol. 769, Himmel et al, eds, American Chemical Society: Washington DC (2001).

M.P. Coughlan. Staining Techniques for the Detection of th eindividual Components of Cellulolytic Enzyme Systems. Methods in Enzymology, vol. 160. 1988.

K. Herbers et al. A Thermostable Xylanase from *Clostridium thermocellum* Expressed at High Levels in the Apoplasty os Trangenic Tobacca Has No Detrimental Effects and is easily Purified. Bio/Technology vol. 13 Jan. 1995.

Hood et al. "Industrial Proteins produced from Transgenic Plants" *Plants as Factories for Protein Production* Hood, Howard edits., Luwer Publishing (2002) pp. 119-135.

PCT report from PCT/US02/38763.

* cited by examiner

Figure 2

E1 cellulase gene sequence

GCCGGCGGTGGCTACTGGCACACCAGCGGCAGGGAGATCCTGGACGCCAAC
AATGTGCCGGTGAGGATCGCCGGCATCAACTGGTTTGGGTTCGAAACCTGCA
ATTACGTCGTGCACGGTCTCTGGTCACGCGACTACCGCAGCATGCTCGACCA
GATAAAGTCGCTCGGCTACAACACAATCCGGCTGCCGTACTCTGACGACATT
CTCAAGCCGGGCACCATGCCGAACAGCATCAATTTTTACCAGATGAATCAGG
ACCTGCAGGGTCTGACGTCCTTGCAGGTCATGGACAAAATCGTCGCGTACGC
CGGTCAGATCGGCCTGCGCATCATTCTTGACCGCCACCGACCGGATTGCAGC
GGGCAGTCGGCGCTGTGGTACACGAGCAGCGTCTCGGAGGCTACGTGGATTT
CCGACCTGCAAGCGCTGGCGCAGCGCTACAAGGGAAACCCGACGGTCGTCG
GCTTTGACTTGCACAACGAGCCGCATGACCCGGCCTGCTGGGGCTGCGGCGA
TCCGAGCATCGACTGGCGATTGGCCGCCGAGCGGGCCGGAAACGCCGTGCTC
TCGGTGAATCCGAACCTGCTCATTTTCGTCGAAGGTGTGCAGAGCTACAACG
GAGACTCCTACTGGTGGGGCGGCAACCTGCAAGGAGCCGGCCAGTACCCGGT
CGTGCTGAACGTGCCGAACCGCCTGGTGTACTCGGCGCACGACTACGCGACG
AGCGTCTACCCGCAGACGTGGTTCAGCGATCCGACCTTCCCCAACAACATGC
CCGGCATCTGGAACAAGAACTGGGGATACCTCTTCAATCAGAACATTGCACC
GGTATGGCTGGGCGAATTCGGTACGACACTGCAATCCACGACCGACCAGACG
TGGCTGAAGACGCTCGTCCAGTACCTACGGCCGACCGCGCAATACGGTGCGG
ACAGCTTCCAGTGGACCTTCTGGTCCTGGAACCCCGATTCCGGCGACACAGG
AGGAATTCTCAAGGATGACTGGCAGACGGTCGACACAGTAAAAGACGGCTAT
CTCGCGCCGATCAAGTCGTCGATTTTCGATCCTGTCGGCGCGTCTGCATCGCC
TAGCAGTCAACCGTCCCCGTCGGTGTCGCCGTCTCCGTCGCCGAGCCCGTCGG
CGAGTCGGACGCCGACGCCTACTCCGACGCCGACAGCCAGCCCGACGCCAAC
GCTGACCCCTACTGCTACGCCCACGCCCACGGCAAGCCCGACGCCGTCACCG
ACGGCAGCCTCCGGAGCCCGCTGCACCGCGAGTTACCAGGTCAACAGCGATT
GGGGCAATGGCTTCACGGTAACGGTGGCCGTGACAAATTCCGGATCCGTCGC
GACCAAGACATGGACGGTCAGTTGGACATTCGGCGGAAATCAGACGATTACC
AATTCGTGGAATGCAGCGGTCACGCAGAACGGTCAGTCGGTAACGGCTCGGA
ATATGAGTTATAACAACGTGATTCAGCCTGGTCAGAACACCACGTTCGGATT
CCAGGCGAGCTATACCGGAAGCAACGCGGCACCGACAGTCGCCTGCGCAGC
AAGTTAA

Figure 4A

Vacuole targeting sequence

ATGGCCCACGCCCGCGTCCTCCTCCTGGCGCTCGCCGTCCTGGCCACGGCCGC
CGTCGCCGTCGCCTCCTCCTCCTCCTTCGCCGACTCCAACCCGATCCGGCCGG
TCACCGACCGCGCCGCGTCCACC

Figure 4B

Barley alpha amylase signal sequence

ATGGCGAACAAGCACCTGAGCCTTAGCCTCTTCCTCGTGCTCCTGGGCCTCTC
CGCCTCCCTCGCCTCCGGC

Figure 6

CBH I gene sequence

CAGAGCGCCTGCACCCTGCAGAGCGAGACCCACCCGCCACTGACCTGGCAGA
AATGCTCGTCTGGTGGCACGTGCACTCAACAGACAGGCTCCGTGGTCATCGA
CGCCAACTGGCGCTGGACTCACGCTACGAACAGCAGCACGAACTGCTACGAT
GGCAACACTTGGAGCTCGACCCTATGTCCTGACAACGAGACCTGCGCGAAGA
ACTGCTGTCTGGACGGTGCCGCCTACGCGTCCACGTACGGAGTTACCACGAG
CGGTAACAGCCTCTCCATTGGCTTTGTCACCCAGTCTGCGCAGAAGAACGTTG
GCGCTCGCCTTTACCTTATGGCGAGCGACACGACCTACCAGGAATTCACCCT
GCTTGGCAACGAGTTCTCTTTCGATGTTGATGTTTCGCAGCTGCCGTGCGGCT
TGAACGGAGCTCTCTACTTCGTGTCCATGGACGCGGATGGTGGCGTGAGCAA
GTATCCCACCAACACCGCTGGCGCCAAGTACGGCACGGGGTACTGTGACAGC
CAGTGTCCCCGCGATCTGAAGTTCATCAATGGCCAGGCCAACGTTGAGGGCT
GGGAGCCGTCATCCAACAACGCGAACACGGGCATTGGAGGACACGGAAGCT
GCTGCTCTGAGATGGATATCTGGGAGGCCAACTCCATCTCCGAGGCTCTTACC
CCCCACCCTTGCACGACTGTCGGCCAGGAGATCTGCGAGGGTGATGGGTGCG
GCGGAACTTACTCCGATAACAGATATGGCGGCACTTGCGATCCCGATGGCTG
CGACTGGAACCCATACCGCCTGGGCAACACCAGCTTCTACGGCCCTGGCTCA
AGCTTTACCCTCGATACCACCAAGAAATTGACCGTTGTCACCCAGTTCGAGA
CGTCGGGTGCCATCAACCGATACTATGTCCAGAATGGCGTCACTTTCCAGCA
GCCCAACGCCGAGCTTGGTAGTTACTCTGGCAACGAGCTCAACGATGACTAC
TGCACAGCTGAGGAGGCAGAATTCGGCGGATCCTCTTTCTCAGACAAGGGCG
GCCTGACTCAGTTCAAGAAGGCTACCTCTGGCGGCATGGTTCTGGTCATGAGT
CTGTGGGATGACTACTACGCCAACATGCTGTGGCTGGACTCCACCTACCCGA
CAAACGAGACCTCCTCCACACCCGGTGCCGTGCGCGGAAGCTGCTCCACCAG
CTCCGGTGTCCCTGCTCAGGTCGAATCTCAGTCTCCCAACGCCAAGGTCACCT
TCTCCAACATCAAGTTCGGACCCATTGGCAGCACCGGCAACCCTAGCGGCGG
CAACCCTCCCGGCGGAAACCCGCCTGGCACCACCACCACCCGCCGCCCAGCC
ACTACCACTGGAAGCTCTCCCGGACCTACCCAGTCTCACTACGGCCAGTGCG
GCGGTATTGGCTACAGCGGCCCCACGGTCTGCGCCAGCGGCACAACTTGCCA
GGTCCTGAACCCTTACTACTCTCAGTGCCTGTAA

Ear of corn from an event

Ear of corn from an event – highest expressing seed

Figure 15 cel7D/cbh1-4 sequence

*atggcgaacaagcacctctccctgagcctcttcctggtgctcctgggcctctccgcgagcctggcctccgggcaacaggctggcaccaacacgg
cggagaaccaccccagctccagtcgcagcagtgcacgacgagcggcggctgcaagccgttgagcacgaaggtcgtcctcgactcgaactggc
gctgggtccacagcacctcgggctacaccaactgctacaccggcaacgagtgggacacctcgctctgccccgacggcaagacatgcgccgcga
actgcgcgctcgacggtgcggactactctggcacctacggtatcacctccaccggcaccgcgctcacgctcaagtttgtcacgggctccaatgtcg
gctcccgcgtctacctcatggcggatgatacgcactaccagctgctcaagctcctgaaccaggagttcacctttgacgtcgacatgtccaacctcccc
tgcggtctcaacggcgcgctctacctctccgcgatggacgccgacggtggcatgtcgaagtacccggaaacaaggctggtgccaagtacggaa
ctggttactgcgactcgcagtgcccgaaggacatcaagttcattaacggcgaggctaatgtcggcaactggaccgagaccggcagcaacaccggt
acgggcagctacggtacctgctgcagcgagatggacatatgggaggccaacaacgatgccgctgctttcactccccacccttgcaccaccaccgg
tcagacccgttgctctggggatgactgcgcgcgtaacaccggtctttgcgacggtgacggctgcgatttcaactcgttccgcatgggtgacaagacc
ttcctcggcaaggggatgaccgtcgacacctccaagcccttcaccgtcgtcacccagttcctgaccaacgacaacacctccaccggcacgctctct
gagatccgccgcatctacattcagaacggcaaggtcatccagaactcggtcgcgaacatccccggtgtcgaccccgtcaacagcatcaccgacaa
cttctgcgcgcagcagaagaccgcgttcggcgacaccaactggttcgcgcagaagggcggcctgaagcagatgggcgaggccctcggcaacg
gcatggtcctcgctctctcgatctgggacgaccacgccgcgaacatgctctggctcgactccgactacccgaccgacaaggacccgtccgccccc
ggtgtcgcgcgcggcacgtgcgcgaccacctcgggtgtcccctccgacgtcgagtcccaggtgcccaactcccaggtcgtcttctccaacatcaa
gttcggcgacatcggcagcaccttcagcggcacctcctcccccaacccgccaggcggctccaccacctcctcgcccgtcaccaccagccctacgc
ccccgcccacaggcccgaccgtccctcagtggggtcagtgcggtggtattggctactctggctcgactacctgcgccagcccgtacacttgccacg
tcctcaaccccttactactcgcagtgctac*

Figure 16 extended globulin-1 promoter cggtatgaatttggaaacaaattcagtacttttaaaaaaatttgttgtagggagcaaataatacataaaataatttatgcattattttatttttatttgtaataat
atgcttgaaacgataattcagtatgcatgttgtgccagtgtactacacgggcggggggaggggattgagtgggccagcgcggtgcgtagggtagat
gggctgaaattgataactcaagtccgactaggttctcttttatttcccttccttttctattttccttctttaattttcatgctttcaaactaaattcaaattcgagt
tttgaatttcagcttctaaattgtacactaaaattatatgataaggtaaccccctactattacttttaatttttttattctaccccatattgtttacttaggggagaat
aattgacttaatcacattcttcctaggtttcaattctcaatcttcaaatccacattttagatttctattttgaatttaaataccagtttggatttagagttcaatttc
aaaatacacaaccaaaataccagcatgaatgcaaatatattttatgtttatgtatttacttttcttttatactttgctcaaaatagttattttcatgtatgaaactc
aataagcaaggaactcacgttattatataacctaataggaataatttaggtaacataatttatcatcctcttgatttaaaagagatatgcctccagaataag
acacatactaaaaataactctaatattgaataactaaagtcgtacaaatctctactattattcctataaaataataaagaactagctacaacttctttaaggc
attattcagggtttacagcttgagaggcatgaacccatcctgtatactcctggacttggaagacaaaatgtcaaccaaagtgaaaggttttcttatggttg
ctgctaagagatagattgaacactagatctctctcctaagacgtcagggcatgcgtttagactcctacacatgcgaaaactgcatcttacagttggaagaa
actatatctcaccacttcctgcggtgtaactttgcccaaagatgttggctcactgttggaatcactccgccccgaactttggatctaacgcttgcagtgct
acatattagagcaagactaacaatgccgtggagaatggaaggtattataaccatgtcatggtgcatatggaaatgtcgaaataactggatattcgaaaa
cataccgccaacggtggcggcctgcaaggaaatgttcaagactgaaatgaactacatctgctaccaagttaagctcgagacaggagctaaaagtag
aaactggatacaacactttgtaacatagtgacactcccctttccttctttaacttagaactatacatacaatccacattcaataaaaatttgtaggtacgc
catacacactaccggaatccggctctttgccgagtgtgaggcgctttgtcgagtgcttttgtccagcactcggcaaaaaagtctttgccatgtgccgc
actcggcaaagtcctgctctcggtaacgaccgcgtttaccgagagcaggactctcgacacagaaatacactcgacaaagaaatctttgccgagagc
caaacactcggcgaacggcagcgctcggcaaagggtcgtcagccgccgtctaaagctgacggtcgttatctttgtcgagtgcccctcgtccgaca
ctcagtagagcaagcttgccgagtgccatccttggacactcgataaagtatattttatttttttttattttgccaaccaaacttttgtggtatgttcctacacta
tgtagatctacatgtaccattttggcacaattacaaaaatgttttctataactattagatttagttcgtttatttgaatttcttcggaaaattcacatatgaactgc
aagtcactcgaaacatgaaaaaccgtgcatgcaaaataaatgatatgcatgttatctagcacaagttacgaccgaattcagaagcagaccagaatctt
caagcaccatgctcactaaacatgaccgtgaacttgttatccagttgtttaaaaattgtataaaacacaaataaagtcagaaattaatgaaacttgtccac
atgtcatgatatcatatatagaggttgtgataaaaatttgataatgtttcggtaaagttgtgacgtactatgtgtagaaacctaagtgacctacacataaaat
catagagtttcaatgtagttcactcgacaaagactttgtcaagtgtccgataaaaagtattcagcaaagaagccgttgtcgatttactgttcgtcgagatc
tctttgccgagtgtcacactaggcaaagtctttacggagtgttttcaggctttgacactcggcaaagcgctcgattccagtagtgacagtaatttgcatc
aaaaatagccgagagatttaaaatgagtcaactaatagaccaactaattattagctattagtcgttagcttctttaatctaagctaaaaccaactaatagct
tatttgttgaattacaattagctcaacgtgaattctctgttttttctataaaaaaaagggaaactgcccctcatttacagcaaactgtccgctgcctgtcgtcc
agatacaatgaacgtacctagtaggaactcttttacacgctcggtcgctcgccgcggatcggagtcccaggaacacgacaccactgtggaacacga
caaagtctgctcagaggcggccacaccctggcgtgcaccgagccggagcccggataagcacggtaaggagagtacgcgcgggacgtggcgacc
cgtgtgtctgctgccacgcagccttcctccacgtagccgcgcggccgcgccacgtaccagggcccggcgctggtataaatgcgcgccacctccgc
tttagttctgcatacagccaacccaacacacacccgagcatatcacagtgacagacactacacgATG

Figure 18 cel5A sequence

*Atggcgaacaagcacctctccctgagcctcttcctggtgctcctgggcctctccgcgagcctggcctccgggcagcagcaacaatgggggtcaat
gtggtggtattggatggactggcgccacgacttgcgtagctggctccgtctgctccgtcttgaacccttactactcccagtgcatccctggcgctgcca
cggtcacctcttcaagcgcgccgtccactccaactcccccgctggtgctcttcctcgtcttggaggtgtgaacacggctggctatgacttcagcgttg
ctacagatggtagcttcacaggcaccggtgtctcccctccagtctctcaattctcccacttctcgtctcagggcgcgaacctgtatcgtattcctttcgcc
tggcagctcatgactcctaccctcggcggtaccatcagccaaagtttcctgtctcgctatgaccagaccgtccaagccgccttgaactccggtcccaa
cgtcttcgtcatcatcgacctgcacaactacgcgcgctggaacgggggcatcattgctcagggtggtcccaccgacgcccagttccagagcatctg
gactcagctcgctcagaagtatggcagcaaccagcgcgtcattttcggcatcatgaacgagccgcacgatattccttctatctcgacctgggtcaact
ccgtgcaaggagctgtcaacgctatccgcgccgccggagctacgaactacctccttcttccaggcagcagctggtcgtctgcacaagcgttcccca
ccgaggccggcccccctcctcgttaaggttacggatcctctcggcggcaccagcaagttgatctttgatgttcacaagtacctggacagcgataacagt
ggcactcaccctgactgcaccaccgacaacgtccaggtcctccagacccttgtccaattcttgcaggccaacggcaataggcaggccatcctcagt
gaaaccggaggaggcaacacctctagctgcgagtctctccttgcaaatgaactcgcctacgtcaagtctgcttaccccactcttgctggtttctccgtct
gggccgctggtgcctttgataccacctacgttctcactgttaccccgaacgctgacggttctgaccaacctctctgggttgacgctgtaaagcccaacc
ttcctaaggacgagctc*

Figure 20

*P. chrysosporium* CBH I sequence atggcgaacaagcacctctccctgagcctcttcctggtgctcctgggcctctccgcgagcctggcctccggggcctgcactctgaccgctgagaa
ccacccctcgctgacgtggtccaagtgcacgtctggcggcagctgcaccagcgtccagggttccatcaccatcgacgccaactggcggtggactc
accggaccgatagcgccaccaactgctacgagggcaacaagtgggatacttcgtactgcagcgatggtccttcttgcgcctccaagtgctgcatcg
acggcgctgactactcgagcacctatggcatcaccacgagcggtaactccctgaacctcaagttcgtcaccaagggccagtactcgaccaacatcg
gctcgcgtacctacctgatggagagcgacaccaagtaccagatgttccagctcctcggcaacgagttcaccttcgatgtcgacgtctccaacctcgg
ctgcggcctcaatggcgccctctacttcgtgtccatggatgccgatggtggcatgtccaagtactcgggcaacaaggcaggtgccaagtacggtac
cggctactgtgattctcagtgcccccgcgacctcaagttcatcaacggcgaggccaacgtagagaactggcagagctcgaccaacgatgccaacg
ccggcacgggcaagtacggcagctgctgctccgagatggacgtctgggaggccaacaacatggccgccgccttcactcccacccttgcnccgt
gatcggccagtcgcgctgcgagggcgactcgtgcggcggtacctacagcaccgaccgctatgccggcatctgcgaccccgacggatgcgacttc
aactcgtaccgccagggcaacaagaccttctacggcaagggcatgacggtcgacacgaccaagaagatcacggtcgtcacccagttcctcaaga
actcggccggcgagctctccgagatcaagcggttctacgtccagaacggcaaggtcatccccaactccgagtccaccatcccgggcgtcgaggg
caactccatcacccaggactggtgcgaccgccagaaggccgccttcggcgacgtgaccgacttncaggacaagggcggcatggtccagatggg
caaggccctcgcggggcccatggtcctcgtcatgtccatctgggacgaccacgccgtcaacatgctctggctcgactccacctggcccatcgacgg
cgccggcaagccgggcgccgagcgcggtgcctgccccaccacctcgggcgtccccgctgaggtcgaggccgaggccccaactccaacgtca
tcttctccaacatccgcttcggccccatcggctccaccgtctccggcctgcccgacggcggcagcggcaacccccaacccgcccgtcagctcgtcc
accccggtcccctcctcgtccaccacatcctccggttcctccggcccgactggcggcacgggtgtcgctaagcactatgagcaatgcggaggaatc
gggttcactggccctacccagtgcgagagcccctacacttgcaccaagctgaatgactggtactcgcagtgcctg

Figure 22

EG5 sequence

*atggcgaacaagcacctctccctgagcctcttcctggtgctcctgggcctctccgcgagcctggcctccgggc*agctctcgggcagcggccaga
cgacccggtactgggactgctgcaagccgagctgcgcctggcccggcaagggcccctcgtctccggtgcaggcctgcgacaagaacgacaacc
cgctcaacgacggcggctccacccggtccggctgcgacgcgggcggcagcgcctacatgtgctcctcccagagcccctgggccgtcagcgacg
agctgtcgtacggctgggcggccgtcaagctcgccggcagctccgagtcgcagtggtgctgcgcctgctacgagctgaccttcaccagcgggcc
ggtcgcgggcaagaagatgattgtgcaggcgaccaacaccggtggcgacctgggcgacaaccactttgacctggccatccccggtggcggtgtc
ggtattttcaacgcctgcaccgaccagtacggcgctcccccgaacggctggggcgaccgctacggcggcatccattccaaggaagagtgcgaatc
cttcccggaggccctcaagcccggctgcaactggcgcttcgactggttccaaaacgccgacaacccgtcggtcaccttccaggaggtggcctgcc
cgtcggagctcacgtccaagagcggctgctcccgtaaggacgagctc

SEQUENCE LISTING

<160> NUMBER OF SEQ ID NOS: 12

<210> SEQ ID NO 1
<211> LENGTH: 1566
<212> TYPE: DNA
<213> ORGANISM: Acidothermus cellulolyticus

<400> SEQUENCE: 1

```
gccggcggtg gctactggca caccagcggc agggagatcc tggacgccaa caatgtgccg      60
gtgaggatcg ccggcatcaa ctggtttggg ttcgaaacct gcaattacgt cgtgcacggt     120
ctctggtcac gcgactaccg cagcatgctc gaccagataa agtcgctcgg ctacaacaca     180
atccggctgc cgtactctga cgacattctc aagcccggca ccatgccgaa cagcatcaat     240
ttttaccaga tgaatcagga cctgcagggt ctgacgtcct gcaggtcat ggacaaaatc      300
gtcgcgtacg ccggtcagat cggcctgcgc atcattcttg accgccaccg accggattgc     360
agcgggcagt cggcgctgtg gtacacgagc agcgtctcgg aggctacgtg gatttccgac     420
ctgcaagcgc tggcgcagcg ctacaaggga acccgacgg tcgtcggctt tgacttgcac       480
aacgagccgc atgacccggc ctgctggggc tgcggcgatc cgagcatcga ctggcgattg     540
gccgccgagc gggccggaaa cgccgtgctc tcggtgaatc cgaacctgct cattttcgtc     600
gaaggtgtgc agagctacaa cggagactcc tactggtggg gcggcaacct gcaaggagcc     660
ggccagtacc cggtcgtgct gaacgtgccg aaccgcctgg tgtactcggc gcacgactac     720
gcgacgagcg tctacccgca cgacgtggttc agcgatccga ccttccccaa caacatgccc     780
ggcatctgga caagaactg gggataacctc ttcaatcaga acattgcacc ggtatggctg     840
ggcgaattcg gtacgacact gcaatccacg accgaccaga cgtggctgaa gacgctcgtc     900
cagtacctac ggccgaccgc gcaatacggt gcggacagct ccagtgtgac cttctggtcc     960
tggaaccccg attccggcga cacaggagga attctcaagg atgactggca gacggtcgac    1020
acagtaaaag acggctatct cgcgccgatc aagtcgtcga ttttcgatcc tgtcggcgcg    1080
tctgcatcgc ctagcagtca accgtccccg tcggtgtcgc cgtctccgtc gccgagcccg    1140
tcggcgagtc ggacgccgac gcctactccg acgccgacag ccagcccgac gccaacgctg    1200
accctactg ctacgcccac gcccacggca agcccgacgc cgtcaccgac ggcagcctcc     1260
ggagcccgct gcaccgcgag ttaccaggtc aacagcgatt ggggcaatgg cttcacggta    1320
acggtggccg tgacaaattc cggatccgtc gcgaccaaga catggacggt cagttggaca    1380
ttcggcggaa atcagacgat taccaattcg tggaatgcag cggtcacgca gaacggtcag    1440
tcggtaacgg ctcggaatat gagttataac aacgtgattc agcctggtca gaacaccacg    1500
ttcggattcc aggcgagcta taccggaagc aacgcggcac cgacagtcgc ctgcgcagca    1560
agttaa                                                               1566
```

<210> SEQ ID NO 2
<211> LENGTH: 129
<212> TYPE: DNA
<213> ORGANISM: Hordeum vulgare

<400> SEQUENCE: 2

```
atggcccacg cccgcgtcct cctcctggcg ctcgccgtcc tggccacggc cgccgtcgcc      60
gtcgcctcct cctcctcctt cgccgactcc aacccgatcc ggccggtcac cgaccgcgcc    120
gcgtccacc                                                             129
```

<210> SEQ ID NO 3
<211> LENGTH: 72
<212> TYPE: DNA
<213> ORGANISM: Hordeum vulgare

<400> SEQUENCE: 3
atggcgaaca agcacctgag ccttagcctc ttcctcgtgc tcctgggcct ctccgcctcc    60
ctcgcctccg gc                                                        72

<210> SEQ ID NO 4
<211> LENGTH: 1494
<212> TYPE: DNA
<213> ORGANISM: Trichodesmium sp.

<400> SEQUENCE: 4
cagagcgcct gcaccctgca gagcgagacc cacccgccac tgacctggca gaaatgctcg    60
tctggtggca cgtgcactca acagacaggc tccgtggtca tcgacgccaa ctggcgctgg   120
actcacgcta cgaacagcag cacgaactgc tacgatggca cacttggag ctcgacccta    180 tgtcctgaca cgagacctg cgcgaagaac tgctgtctgg acggtgccgc ctacgcgtcc    240
acgtacggag ttaccacgag cggtaacagc ctctccattg ctttgtcac ccagtctgcg    300 cagaagaacg ttggcgctcg cctttacctt atggcgagcg cacgaccta ccaggaattc    360 accctgcttg gcaacgagtt ctctttcgat gttgatgttt cgcagctgcc gtgcggcttg    420
aacggagctc tctacttcgt gtccatggac gcggatggtg gcgtgagcaa gtatcccacc    480
aacaccgctg gcgccaagta cggcacgggg tactgtgaca gccagtgtcc ccgcgatctg    540
aagttcatca atggccaggc caacgttgag ggctgggagc cgtcatccaa caacgcgaac    600
acgggcattg gaggacacgg aagctgctgc tctgagatgg atatctggga ggccaactcc    660
atctccgagg ctcttacccc ccaccccttgc acgactgtcg gccaggagat ctgcgagggt    720
gatgggtgcg gcggaactta ctccgataac agatatggcg gcacttgcga tcccgatggc    780
tgcgactgga acccataccg cctgggcaac accagcttct acggccctgg ctcaagcttt    840
accctcgata ccaccaagaa attgaccgtt gtcacccagt cgagacgtc gggtgccatc    900 aaccgatact atgtccagaa tggcgtcact ttccagcagc ccaacgccga gcttggtagt    960
tactctggca acgagctcaa cgatgactac tgcacagctg aggaggcaga attcggcgga   1020 tcctcttct cagacaaggg cggcctgact cagttcaaga aggctacctc tggcggcatg   1080
gttctggtca tgagtctgtg gatgactac tacgccaaca tgctgtggct ggactccacc   1140
tacccgacaa acgagacctc ctccacaccc ggtgccgtgc gcggaagctg ctccaccagc   1200
tccggtgtcc ctgctcaggt cgaatctcag tctcccaacg ccaaggtcac cttctccaac   1260
atcaagttcg accccattgg cagcaccggc aaccctagcg gcggcaaccc tcccggcgga   1320
aacccgcctg gcaccaccac caccgccgc ccagccacta ccactggaag ctctcccgga   1380
cctacccagt ctcactacgg ccagtgcggc ggtattggct acagcggccc cacggtctgc   1440
gccagcggca caacttgcca ggtcctgaac ccttactact ctcagtgcct gtaa         1494

<210> SEQ ID NO 5
<211> LENGTH: 72
<212> TYPE: DNA
<213> ORGANISM: Hordeum vulgare

<400> SEQUENCE: 5
atggcgaaca agcacctctc cctgagcctc ttcctggtgc tcctgggcct ctccgcgagc    60

```
ctggcctccg gg                                                         72
```

<210> SEQ ID NO 6
<211> LENGTH: 1548
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 6

```
atggcgaaca agcacctctc cctgagcctc ttcctggtgc tcctgggcct ctccgcgagc    60
ctggcctccg ggcaacaggc tggcaccaac acggcggaga ccaccccca gctccagtcg    120
cagcagtgca cgacgagcgg cggctgcaag ccgttgagca cgaaggtcgt cctcgactcg    180
aactggcgct gggtccacag cacctcgggc tacaccaact gctacaccgg caacgagtgg    240
gacacctcgc tctgccccga cggcaagaca tgcgccgcga actgcgcgct cgacggtgcg    300
gactactctg gcacctacgg tatcacctcc accggcaccg cgctcacgct caagtttgtc    360
acgggctcca atgtcggctc ccgcgtctac ctcatggcgg atgatacgca ctaccagctg    420
ctcaagctcc tgaaccagga gttcacctt gacgtcgaca tgtccaacct ccctgcggt    480
ctcaacggcg cgctctacct ctccgcgatg gacgccgacg gtggcatgtc gaagtacccc    540
ggaaacaagg ctggtgccaa gtacggaact ggttactgcg actcgcagtg cccgaaggac    600
atcaagttca ttaacggcga ggctaatgtc ggcaactgga ccgagaccgg cagcaacacc    660
ggtacgggca gctacggtac ctgctgcagc gagatggaca tatgggaggc caacaacgat    720
gccgctgctt tcactcccca cccttgcacc accaccggtc agacccgttg ctctggggat    780
gactgcgcgc gtaacaccgg tctttgcgac ggtgacggct gcgatttcaa ctcgttccgc    840
atgggtgaca gaccttcct cggcaagggg atgaccgtcg acacctccaa gcccttcacc    900
gtcgtcaccc agttcctgac caacgacaac acctccaccg gcacgctctc tgagatccgc    960
cgcatctaca ttcagaacgg caaggtcatc cagaactcgg tcgcgaacat ccccggtgtc    1020
gaccccgtca acagcatcac cgacaacttc tgcgcgcagc agaagaccgc gttcggcgac    1080
accaactggt tcgcgcagaa gggcggcctg aagcagatgg gcgaggccct cggcaacggc    1140
atggtcctcg ctctctcgat ctgggacgac cacgccgcga acatgctctg gctcgactcc    1200
gactacccga ccgacaagga cccgtccgcc cccggtgtcg cgcgcggcac gtgcgcgacc    1260
acctcgggtg tcccctccga cgtcgagtcc caggtgccca ctccaggt cgtcttctcc    1320
aacatcaagt tcggcgacat cggcagcacc ttcagcggca cctcctcccc caacccgcca    1380
ggcggctcca ccacctcctc gcccgtcacc accagcccta cgcccccgcc cacaggcccg    1440
accgtccctc agtggggtca gtgcggtggt attggctact ctggctcgac tacctgcgcc    1500
agcccgtaca cttgccacgt cctcaaccct tactactcgc agtgctac              1548
```

<210> SEQ ID NO 7
<211> LENGTH: 3006
<212> TYPE: DNA
<213> ORGANISM: Zea mays

<400> SEQUENCE: 7

```
cggtatgaat ttggaaacaa attcagtact tttaaaaaaa tttgttgtag ggagcaaata    60
atacataaaa taatttatgc attatttat tttttatttg taataatatg cttgaaacga    120
taattcagta tgcatgttgt gccagtgtac tacacgggcg gggggagggg attgagtggg    180
ccagcgcggt gcgtagggta gatgggctga aattgataac tcaagtccga ctaggttctc    240
```

```
tttttatttc ccttccttttt ctattttcct ttcttttaat tttcatgctt tcaaactaaa    300
ttcaaattcg agttttgaat ttcagcttct aaattgtaca ctaaaattat atgataaggt    360 aaccccctact attacttttta atttttttat tctaccccat attgtttact tagggagaa    420 taattgactt aatcacattc ttcctaggtt tcaattctca atctttcaaa tccacatttt    480
tagatttcta ttttgaattt aaataccagt ttggatttag agttcaattt caaaatacac    540
aaccaaaata ccagcatgaa tgcaaatata ttttatgttt atgtatttac ttttctttta    600
tactttgctc aaaatagtta ttttcatgta tgaaactcaa taagcaagga actcacgtta    660
ttatataacc taataggaat aatttaggta acataattta tcatcctctt gatttaaaag    720
agatatgcct ccagaataag acacatacta aaaataactc taatattgaa taactaaagt    780
cgtacaaatc tctactatta ttcctataaa ataataaaga actagctaca acttctttaa    840
ggcattattc agggtttaca gcttgagagg catgaaccca tcctgtatac tcctggactt    900
ggaagacaaa atgtcaacca aagtgaaagg ttttcttatg gttgctgcta agagatagat    960
tgaacactag atctctccta agacgtcagg gcatgcgttt agactcctac acatgcgaaa   1020
actgcatctt acagttggaa gaaactatat ctcaccactt cctgcggtgt aactttgccc   1080
aaagatgttg gctcactgtt ggaatcactc cgccccgaac tttggatcta acgcttgcag   1140
tgctacatat tagagcaaga ctaacaatgc cgtggagaat ggaaggtatt ataaccatgt   1200
catggtgcat atggaaatgt cgaataact ggatattcga aaacataccg ccaacggtgg   1260
cggcctgcaa ggaaatgttc aagactgaaa tgaactacat ctgctaccaa gttaagctcg   1320
agacaggagc taaaagtaga aactggatac aacactttgt aacatagtga cactccccctt  1380 ttcctttctt ttaccttaga actatacata caatccacat tcaataaaaa tttgtaggta   1440
cgccatacac actaccggaa tccggctctt tgccgagtgt gaggcgcttt gtcgagtgct   1500
ttttgtccag cactcggcaa aaaagtcttt gccatgtgcc gcactcggca aagtcctgct   1560
ctcggtaacg accgcgttta ccgagagcag gactctcgac acagaaatac actcgacaaa   1620
gaaatctttg ccgagagcca aacactcggc gaacggcagc gctcggcaaa gggtcgtcag   1680
ccgccgtcta aagctgacgg tcgttatctt tgtcgagtgc cccctcgtcc gacactcagt   1740
agagcaagct tgccgagtgc catccttgga cactcgataa agtatatttt attttttttt   1800
attttgccaa ccaaactttt tgtggtatgt tcctacacta tgtagatcta catgtaccat   1860
tttggcacaa ttacaaaaat gttttctata actattagat ttagttcgtt tatttgaatt   1920
tcttcggaaa attcacatat gaactgcaag tcactcgaaa catgaaaaac cgtgcatgca   1980
aaataaatga tatgcatgtt atctagcaca agttacgacc gaattcagaa gcagaccaga   2040
atcttcaagc accatgctca ctaaacatga ccgtgaactt gttatccagt tgtttaaaaa   2100
ttgtataaaa cacaaataaa gtcagaaatt aatgaaactt gtccacatgt catgatatca   2160
tatatagagg ttgtgataaa aatttgataa tgtttcggta aagttgtgac gtactatgtg   2220
tagaaaccta agtgacctac acataaaatc atagagtttc aatgtagttc actcgacaaa   2280
gactttgtca agtgtccgat aaaaagtatt cagcaaagaa gccgttgtcg atttactgtt   2340
cgtcgagatc tctttgccga gtgtcacact aggcaaagtc tttacggagt gttttcagg   2400 ctttgacact cggcaaagcg ctcgattcca gtagtgacag taatttgcat caaaaatagc   2460
cgagagattt aaaatgagtc aactaataga ccaactaatt attagctatt agtcgttagc   2520
ttctttaatc taagctaaaa ccaactaata gcttatttgt tgaattacaa ttagctcaac   2580
ggaattctct gttttttcta taaaaaaaag ggaaactgcc cctcatttac agcaaactgt   2640
```

```
ccgctgcctg tcgtccagat acaatgaacg tacctagtag gaactctttt acacgctcgg    2700
tcgctcgccg cggatcggag tcccaggaac acgacaccac tgtggaacac gacaaagtct    2760
gctcagaggc ggccacaccc tggcgtgcac cgagccggag cccggataag cacggtaagg    2820
agagtacggc gggacgtggc gacccgtgtg tctgctgcca cgcagccttc ctccacgtag    2880
ccgcgcggcc gcgccacgta ccagggcccg gcgctggtat aaatgcgcgc cacctccgct    2940
ttagttctgc atacagccaa cccaacacac acccgagcat atcacagtga cagacactac    3000
acgatg                                                                3006
```

<210> SEQ ID NO 8
<211> LENGTH: 1191
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 8

```
atggcgaaca agcacctctc cctgagcctc ttcctggtgc tcctgggcct ctccgcgagc      60
ctggcctccg ggcagcagca acaatggggt caatgtggtg gtattggatg gactggcgcc     120
acgacttgcg tagctggctc cgtctgctcc gtcttgaacc cttactactc ccagtgcatc     180
cctggcgctg ccacggtcac ctcttcaagc gcgccgtcca ctccaactcc ccccgctggt     240
gctcttcctc gtcttggagg tgtgaacacg gctggctatg acttcagcgt tgctacagat     300
ggtagcttca caggcaccgg tgtctcccct ccagtctctc aattctccca cttctcgtct     360
cagggcgcga acctgtatcg tattcctttc gcctggcagc tcatgactcc tacccctcggc    420 ggtaccatca gccaaagttt cctgtctcgc tatgaccaga ccgtccaagc cgccttgaac     480
tccggtccca acgtcttcgt catcatcgac ctgcacaact acgcgcgctg gaacgggggc     540
atcattgctc agggtggtcc caccgacgcc cagttccaga gcatctggac tcagctcgct     600
cagaagtatg gcagcaacca gcgcgtcatt ttcggcatca tgaacgagcc gcacgatatt     660
ccttctatct cgacctgggt caactccgtg caaggagctg tcaacgctat ccgcgccgcc     720
ggagctacga actacctcct tcttccaggc agcagctggt cgtctgcaca agcgttcccc     780
accgaggccg gcccctcct cgttaaggtt acggatcctc tcggcggcac cagcaagttg     840
atctttgatg ttcacaagta cctggacagc gataacagtg gcactcaccc tgactgcacc     900
accgacaacg tccaggtcct ccagacccct gtccaattct gcaggccaa cggcaatagg      960 caggccatcc tcagtgaaac cggaggaggc aacacctcta gctgcgagtc tctccttgca    1020
aatgaactcg cctacgtcaa gtctgcttac cccactcttg ctggtttctc cgtctgggcc    1080
gctggtgcct ttgataccac ctacgttctc actgttaccc cgaacgctga cggttctgac    1140
caacctctct gggttgacgc tgtaaagccc aaccttccta aggacgagct c             1191
```

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
aaggacgagc tc                                                          12
```

<210> SEQ ID NO 10
<211> LENGTH: 1593
<212> TYPE: DNA
<213> ORGANISM: Artificial Sequence
<220> FEATURE:
<223> OTHER INFORMATION: Description of Artificial Sequence: Synthetic nucleotide construct
<220> FEATURE:
<221> NAME/KEY: modified_base
<222> LOCATION: (760)
<223> OTHER INFORMATION: a, c, g, t, unknown, or other
<220> FEATURE:
<221> NAME/KEY: modified_base
<222> LOCATION: (1110)
<223> OTHER INFORMATION: a, c, g, t, unknown, or other

<400> SEQUENCE: 10

```
atggcgaaca agcacctctc cctgagcctc ttcctggtgc tcctgggcct ctccgcgagc      60
ctggcctccg gggcctgcac tctgaccgct gagaaccacc cctcgctgac gtggtccaag     120
tgcacgtctg gcggcagctg caccagcgtc cagggttcca tcaccatcga cgccaactgg     180
cggtggactc accggaccga tagcgccacc aactgctacg agggcaacaa gtgggatact     240
tcgtactgca gcgatggtcc ttcttgcgcc tccaagtgct gcatcgacgg cgctgactac     300
tcgagcacct atggcatcac cacgagcggt aactccctga acctcaagtt cgtcaccaag     360
ggccagtact cgaccaacat cggctcgcgt acctacctga tggagagcga caccaagtac     420
cagatgttcc agctcctcgg caacgagttc accttcgatg tcgacgtctc caacctcggc     480
tgcggcctca atggcgccct ctacttcgtg tccatggatg ccgatggtgg catgtccaag     540
tactcgggca acaaggcagg tgccaagtac ggtaccggct actgtgattc tcagtgcccc     600
cgcgacctca gttcatcaa cggcgaggcc aacgtagaga actggcagag ctcgaccaac     660
gatgccaacg ccggcacggg caagtacggc agctgctgct ccgagatgga cgtctgggag     720
gccaacaaca tggccgccgc ctttcactccc cacccttgcn ccgtgatcgg ccagtcgcgc     780
tgcgagggcg actcgtgcgg cggtacctac agcaccgacc gctatgccgg catctgcgac     840
cccgacggat gcgacttcaa ctcgtaccgc cagggcaaca agaccttcta cggcaagggc     900
atgacggtcg acacgaccaa gaagatcacg gtcgtcaccc agttcctcaa gaactcggcc     960
ggcgagctct ccgagatcaa gcggttctac gtccagaacg gcaaggtcat ccccaactcc    1020
gagtccacca tccgggcgt cgagggcaac tccatcaccc aggactggtg cgaccgccag    1080
aaggccgcct tcggcgacgt gaccgacttn caggacaagg gcggcatggt ccagatgggc    1140
aaggccctcg cggggcccat ggtcctcgtc atgtccatct gggacgacca cgccgtcaac    1200
atgctctggc tcgactccac ctggcccatc gacggcgccg gcaagccggg cgccgagcgc    1260
ggtgcctgcc ccaccacctc gggcgtcccc gctgaggtcg aggccgaggc ccccaactcc    1320
aacgtcatct tctccaacat ccgcttcggc cccatcggct ccaccgtctc cggcctgccc    1380
gacggcggca gcgcaaccc caacccgccc gtcagctcgt ccaccccggt cccctcctcg    1440
tccaccacat cctccggttc ctccggcccg actggcggca cgggtgtcgc taagcactat    1500
gagcaatgcg gaggaatcgg gttcactggc cctacccagt gcgagagccc ctacacttgc    1560
accaagctga atgactggta ctcgcagtgc ctg                                 1593
```

<210> SEQ ID NO 11
<211> LENGTH: 705
<212> TYPE: DNA
<213> ORGANISM: Artificial Sequence
<220> FEATURE:
<223> OTHER INFORMATION: Description of Artificial Sequence: Synthetic nucleotide construct

```
<400> SEQUENCE: 11
atggcgaaca agcacctctc cctgagcctc ttcctggtgc tcctgggcct ctccgcgagc      60
ctggcctccg ggcagctctc gggcagcggc cagacgaccc ggtactggga ctgctgcaag     120
ccgagctgcg cctggcccgg caagggcccc tcgtctccgg tgcaggcctg cgacaagaac     180
gacaacccgc tcaacgacgg cggctccacc cggtccggct gcgacgcggg cggcagcgcc     240
tacatgtgct cctcccagag cccctgggcc gtcagcgacg agctgtcgta cggctgggcg     300
gccgtcaagc tcgccggcag ctccgagtcg cagtggtgct gcgcctgcta cgagctgacc     360
ttcaccagcg ggccggtcgc gggcaagaag atgattgtgc aggcgaccaa caccggtggc     420
gacctgggcg acaaccactt tgacctggcc atccccggtg gcggtgtcgg tattttcaac     480
gcctgcaccg accagtacgg cgctccccccg aacggctggg gcgaccgcta cggcggcatc     540
cattccaagg aagagtgcga atccttcccg gaggccctca gcccggctg caactggcgc     600 ttcgactggt tccaaaacgc cgacaacccg tcggtcacct tccaggaggt ggcctgcccg     660
tcggagctca cgtccaagag cggctgctcc cgtaaggacg agctc                   705

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Asp Glu Leu
  1
```

MONOCOTYLEDONOUS SEED EXPRESSING EXO-1,4B-GLUCANASE

This application claims benefit under 35 U.S.C. §119(e) to previously filed application U.S. Ser. No. 60/607,098, filed Sep. 3, 2004; and is a continuation-in-part of U.S. Ser. No. 10/310,292, filed Dec. 5, 2002, which claims benefit under 35 U.S.C. §119(e) to U.S. Ser. No. 60/340,035, filed Dec. 6, 2001, the contents of all of which are incorporated herein by reference in their entirety.

GOVERNMENT INTEREST

The work of this invention was funded in part by a grant from the USDA and the government has certain rights therein.

FIELD OF THE INVENTION

The present invention relates to commercial production of heterologous proteins in plants. More specifically, the invention is to novel methods of expressing a heterologous polysaccharide degrading enzyme in plants, particularly in grains, and to methods of targeting expression to cell organelles and the cell wall to achieve high levels of expression. Methods of using such enzymes in saccharification methods and in production of ethanol from crop residues are also provided.

BACKGROUND OF THE INVENTION

Polysaccharide degrading enzymes are useful in a variety of applications, such as in animal feed, industrial applications, and, in particular, in ethanol production.

Fossilized hydrocarbon-based energy sources, such as coal, petroleum and natural gas, provide a limited, non-renewable resource pool. Because of the world's increasing population and increasing dependence on energy sources for electricity and heating, transportation fuels, and manufacturing processes, energy consumption is rising at an accelerating rate. The US transportation sector alone consumes over 100 billion gallons of gasoline per year. Most (~60%) of the oil used in the US today is imported, creating a somewhat precarious situation in today's political climate because supply disruptions are highly likely and would cripple the ability of the economy to function. Fossil petroleum resources, on which our standard of living currently depends, will likely be severely limited within the next 50-100 years.

The production of ethanol from lignocellulosic biomass can utilize large volumes of agricultural resources that are untapped today. Ethanol is key to partially replacing petroleum resources, which are limited. Ethanol fuels burn cleanly and because of this, ethanol replacement of petroleum fuels at any ratio will have a positive impact on the environment. Production of ethanol from domestic, renewable sources also ensures a continuing supply. For these reasons, the production of ethanol fuels from lignocellulosic biomass are being developed into a viable industry. High yields of glucose from cellulose (using cellulase enzymes) are required for any economically viable biomass utilization strategy to be realized. The US is one country involved in ethanol production and currently manufactures approximately over three billion gallons of ethanol from corn grain-derived starch. (American Coalition of Ethanol Production, www.ethanol.org; also, Sheehan, J. "The road to bioethanol: A strategic perspective of the US Department of Energy's National Ethanol Program" Himmel M E, Baker J O, Saddler J N eds., *Glycosyl Hydrolases for Biomass Conversion*, 2-25). Ethanol that is produced from corn starch, however, has not been cost-effective alternative to fossil fuels.

Unharvested residues from agricultural crops are estimated at a mass approximately equal to the harvested portion of the crops. Specifically for the corn crop, if half of the residue could be used as a feedstock for the manufacture of ethanol, then about 120 million tons of corn stover would be available annually for biomass conversion processes (Walsh, Marie E. Biomass Feedstock Availability in the United States. State Level Analysis. 1999). Assuming that mature, dry corn stover is approximately 40% cellulose on a dry weight basis then 48 million tons of cellulose/year would be available for hydrolysis to glucose. Using today's technology, a ton of cellulose will yield approximately 100 gallons of ethanol.

Because known technologies for ethanol production from plant biomass have been more costly than the market price for ethanol, ethanol will not become an important alternative to fossil fuels, unless the price of fossil fuels rises substantially. If, however, the cost of the production of ethanol from plant biomass could be reduced, then ethanol might become a cost-effective alternative to fossil fuels even at today's prices for fossil fuels.

Plant biomass is a complex matrix of polymers comprising the polysaccharides cellulose and hemicellulose, and a polyphenolic complex, lignin, as the major structural components. Any strategy designed to substitute lignocellulosic feedstocks for petroleum in the manufacture of fuels and chemicals must include the ability to efficiently convert the polysaccharide components of plant cell walls to soluble, monomeric sugar streams. Cellulose, the most abundant biopolymer on earth, is a simple, linear polymer of glucose. However, its semi-crystalline structure is notoriously resistant to hydrolysis by both enzymatic and chemical means. Yet, high yields of glucose from cellulose are critical to any economically viable biomass utilization strategy.

Nature has developed effective cellulose hydrolytic machinery, mostly microbial in origin, for recycling carbon from plant biomass in the environment. Without it, the global carbon cycle would not function. To date, many cellulase genes have been cloned and sequenced from a wide variety of bacteria, fungi and plants, and many more certainly await discovery and characterization (Schulein, M, 2000. Protein engineering of cellulases. *Biochim. Biophys. Acta* 1543:239-252); Tomme P, et al. 1995. Cellulose Hydrolysis by Bacteria and Fungi. *Advances in Microbial Physiology* 37:1-81). Cellulases are a subset of the glycosyl hydrolase superfamily of enzymes that have been grouped into at least 13 families based on protein sequence similarity, enzyme reaction mechanism, and protein fold motif.

The economics of using corn stover or any other source of lignocellulosic biomass to produce ethanol is ominous at best and is the limiting step behind the attainment of such a goal. The current cost of making ethanol from any source of lignocellulosic biomass with the current enzyme production systems and the biomass collection and pretreatment technology is in the order of about $1.50 per gallon. This is due to the high operation costs of collecting and transporting the lignocellulosic raw material to destination plants, producing the polysaccharide-degrading enzymes and the high cost of pretreating the lignocellulosic raw material to facilitate its enzymatic degradation. To become economical, the processes for ethanol production have to be integrated into the cultivation of agricultural crops. In particular, the process of producing the enzymes required for ethanol production as well as the collection of lignocellulosic raw material have to be integrated into the normal operations of crop cultivation. The crop market will generate the revenues necessary to economically justify its cultivation and the production of ethanol will be a by-product of this operation.

At present enzyme production is primarily by submerged culture fermentation. The scale-up of fermentation systems for the large volumes of enzyme required for biomass conversion would be difficult and extremely capital intensive. For purposes of comparison, a single very large (1 million liter), aerobic fermentation tank could produce 3,091 tons of cellulase protein/yr in continuous culture. Currently, however, fermentation technology is practiced commercially on a significantly smaller scale and in batch mode, so production capacities are closer to 10% of the theoretical 3,091 tons calculated above. Thus, using these assumptions, current practices would yield 3000 times less than the 1.2 MM tons of enzyme needed to convert the cellulose content from 120 MM tons per year of corn stover. Capital and operating costs of such a fermentative approach to producing cellulases are likely to be impractical due to the huge scale and capital investment that will be required.

Several recombinant systems are available for protein production. Foreign proteins have been produced in animal cell cultures and transgenic animals. However, these methods are very expensive and time intensive, particularly in the scale-up of cultures or herds large enough for industrial enzyme production, making them highly impractical. Bacteria and fungi are relatively simple systems but require a large initial investment for capital equipment. On the other hand, crop-based production systems may offer an attractive and cost-effective alternative for industrial enzyme production at the scale required for biomass conversion. Transgenic plants require the lowest capital investment (mainly for dedicated harvesting equipment and storage) of all production systems. The cost of producing crude recombinant protein in plants could be three orders of magnitude lower than that of the mammalian cell system, and 10 fold less than microbial fermentation (Elizabeth E. Hood and Susan L. Woodard. Industrial Proteins Produced from Plants. Molecular Farming. 2002. In: *Plants as Factories for Protein Production*. E E. Hood and J A Howard, Eds., Kluwer Academic Publishers, Dordrecht, The Netherlands pp. 119-135). Advantages of plant systems include the low cost of growing a large biomass, easy scale-up (increase of planted acreage), natural storage organs (tubers, seeds), and established practices for efficient harvesting, transporting, storing and processing of the plant.

Plant systems have been used to express polysaccharide degrading cellulases specifically with varying amounts of success (Table 1). Ziegler et al. (Ziegler, M T, et al. 2000. Accumulation of a thermostable endo-1,4-β-D-glucanase in the apoplast of *Arabidopsis thaliana* leaves. *Molecular Breeding* 6:37-46) have expressed an endoglucanase in *Arabidopsis* leaves and in tobacco tissue culture cells at high levels, but both systems are impractical for commercialization. In addition, some preliminary work has been done with potato (Dai Z, et al. 2000. Improved plant-based production of E1 endoglucanase using potato: expression optimization and tissue targeting. *Molecular Breeding* 6:277-285) but expression levels were relatively low. Studies with tobacco, alfalfa and potato leaves have shown that individual cellulase enzymes can be expressed in these plants (Ziegelhoffer T, et al. 1999. Expression of bacterial cellulase genes in transgenic alfalfa (*Medicago sativa* L.), potato (*Solanum tuberosum* L.) and tobacco (*Nicotiana tabacum* L.). *Molecular Breeding* 5:309-318; and U.S. Pat. No. 5,981,835) although not at levels that would allow economic production of the enzymes.

TABLE 1

Examples of heterologous cellulase expression in plants and production considerations.

| Enzyme | Gene source | Transgenic plant system | Expression level | Stable storage | Scalability[4] |
|---|---|---|---|---|---|
| Endo-1,4-β-D-glucanase | Bacterial (*Acidothermus*) | *Arabidopsis* (cell wall targeted) | 26% TSP in leaves[1] | No | – |
| Endo-1,4-β-D-glucanase | Bacterial (*Acidothermus*) | Potato (cell wall or chloroplast target) | 2.6% TSP[2] in leaves | No | + |
| Endo-1,4-β-D-glucanase | Bacterial (*Thermonospora*) cytosolic localization | Alfalfa (cytosolic localization) | ~0.01% TSP[3] in leaves | No | ++ |
|  |  | Tobacco (cytosolic localization) | 0.1% TSP[3] in leaves | No | + |
| Cellobiohydrolase | Bacterial (*T. fusca*) | Alfalfa (cytosolic localization) | 0.02% TSP[3] in leaves | No | ++ |
|  |  | Tobacco (cytosolic localization) | 0.002% TSP[3] in leaves | No | + |

[1]Zeigler et al., 2000;
[2]Dai et al., 2000;
[3]Ziegelhoffer et al., 1999 and ~% TSP assumes 10% of leaf weight is soluble protein;
[4]Scalability defined by 2002 US crop acreage, scale-up potential: –, unscalable; +, fair; ++, moderate; +++, significant.
TSP = Total soluble protein.

None of the expression systems to date have shown a practical application of producing cellulases. In some of the examples the expression level is much too low to be of any commercial use. The highest level of expression achieved was in *Arabidopsis*. However, the use of this plant is impractical for commercial production of enzymes. It is a model organism, used because of its ease in transformation, but grows to a height of only three inches and could not possibly produce adequate amounts of enzyme for commercial purposes. The volume of material needed and the expression levels need to be such that commercial production is practicable. In general, expression levels should be at least about 0.1% of total soluble protein of the plant tissue used. None of the work to date has involved expression of cellulases in corn (*Zea mays*, L.). While the possiblity of expressing an enzyme to a particular organelle has been presented, and in one instance targeted to the chloroplast (See U.S. Pat. No. 6,429,359) success in increasing expression by targeting specific organelles in plants cells or secreting from cell wall has not been shown. Further, for plant production of the enzymes to be commercially viable, expression at commercial levels in a plant that can be grown, harvested and scaled to commercial quantities must be achieved on a reliable, consistent basis.

Combining these improvements with harvest methods that allow the simultaneous recovery of corn stover and corn grain by a single pass through the field reduces the cost of collecting the lignocellulosic raw material. Such single pass (also referred to as one-pass) harvesting cuts down on the number of times that farm machinery are driven through the fields. This approach minimizes soil compaction, reduces the amount of time invested in material collection and curtails the cost of fossil fuel and labor needed for operating the farm machinery. One-pass harvest is being developed by several groups, for example at Iowa State University by Dr. Graeme Quick. See records and minutes of the "Corn Stover Harvesting Field Demonstration and Biomass Harvesting Colloquium", Harlan, Iowa. Oct. 29, 2001.

Provided by the invention are cost-effective methods for the saccharification of polysaccharides in crop residues. The methods of the invention find particular use in the integration of current practices for the cultivation of crop plants for the purpose of obtaining a commercially desired plant material with the production of commercial levels of polysaccharide degrading enzymes in the tissues of the crop plants and the use of the crop plant residues as a source of lignocellulosic biomass for the production of fermentable sugars.

The methods of the invention find use in transforming crop plants with a nucleotide sequence encoding at least one polysaccharide degrading enzyme, such as those degrading cellulose, hemicellulose or pectin. Any plant tissue expressing the enzyme can be the source of the enzyme. In one embodiment of the invention the same plant used to make the enzyme can be the source of the lignocellulose. The enzymes can be produced in any part of the plant (leaves, seed, roots, etc.) and used for subsequent treatment in degrading polysaccharides of the plant. In an embodiment the crop plant is a plant that produces seeds. The source of the enzyme preferably can be seed tissue, such as one or more of whole seed, hulls, seed coat, endosperm, or embryo (germ). More preferably the seeds have a germ that is capable of being fractioned from the rest of the seed (the term degerminated is sometimes used when referring to separation of the germ) in a commercial milling process. In a preferred embodiment of the invention the enzyme(s) are expressed in the germ portion of the seed. In another preferred embodiment the level of enzymes that are produced in the germ portion of the the seed are at least about 0.1% of the dry weight of the seed.

In particular, the methods of the invention further provide a cost-effective integrated approach to producing fermentable sugars from corn stover that encompasses the production of polysaccharide degrading enzymes in the seeds of genetically engineered corn plants. A portion of or all of the seed can be the source of the degrading enzyme with other plant parts used for other purposes. The option is available to use a select tissue of the seed for commercial purpose, and other tissue used as the source of enzyme for the saccarification process. For example, the corn endosperm can be used as a source of starch, corn stover from the engineered plants as lignocellulosic biomass and embryo as the enzyme source. Further economic advantages are obtained in harvesting the seeds in a first operation and the stover in a second operation such that both operations are carried out concurrently by employing single-pass harvest operations.

The methods of the invention involve producing one or more cell wall polysaccharide-degrading enzymes in a crop plant by transforming the plant with at least one nucleotide construct comprising a nucleotide sequence encoding a cell wall polysaccharide-degrading enzyme operably linked to a promoter that drives expression in the crop plant, more preferably in the crop plant seed or a portion thereof, such that the production of the commercially desired plant material is not forfeited by the production of the enzymes.

The methods further involve obtaining from the transformed plant, tissue that expresses the cell wall polysaccharide-degrading enzyme or enzymes, contacting lignocellulosic biomass with this plant tissue, and exposing the combination to conditions that are favorable for the degradation of cell wall polysaccharides into fermentable sugars. The fermentable sugars can then be utilized for the production of ethanol or other desired molecules using fermentation procedures that are known in the art.

The inventors have devised an integrated method for the economic saccharification of lignocellulosic biomass and its conversion into ethanol. It is, therefore, an object of the present invention to provide cost-effective methods for converting polysaccharides in lignocellulosic biomass into fermentable sugars. It is also an object of the present invention to genetically engineer plants to produce cell wall degrading enzymes at commercially high levels and use such enzymes in saccharification of polysaccharides. A still further object is to obtain both the source of polysaccharides and source of enzymes from one crop. Another object of the invention is to integrate efficient harvest methods such as single pass harvest with the genetic engineering of corn plants to cost effectively produce ethanol from corn stover. A further object of the invention is to produce commercially acceptable levels of polysaccharide-degrading enzymes in corn plants. Yet another object of the invention is to target the expression of polysaccharide-degrading enzymes to corn seeds, preferably to the germ portion of the seed.

In one embodiment of the invention, production of recombinant cellulases in plants is provided that improves over prior attempts to express cellulases in plants in reliability of enzyme production and at commercial levels.

In an embodiment of the invention cellulases are produced in corn plants.

Another object of the invention is the application of large-scale production of cellulases to industrial markets for which it had previously been economically unfeasible to enter.

In yet another embodiment of the invention the cellulases are preferentially expressed to the seed of the plant.

In an embodiment of the invention expression of cellulases is targeted to specific locations within the plant cell in order to increase expression levels of the enzymes in the plant.

Another embodiment of the invention is to express the E1 cellulase (endo-1,4-β-D-glucanase, EC 3.2.1.4) and CBH I (cellobiohydrolase or 1,4-β-D-glucan cellobiosidase, EC 3.2.1.91) in corn. In a further embodiment, the E1 cellulase is secreted to the cell wall, retained in the endoplasmic reticulum or targeted to the vacuole of a plant cell. Another embodiment provides for CBH I enzyme to be secreted to the cell wall or retained in the endoplasmic reticulum.

Other embodiments are to further improve expression of cellulases in plants by backcrossing transgenic plants containing the cellulase expressing gene into plants with good agronomic traits.

SUMMARY OF THE INVENTION

Expression of polysaccharide degrading enzymes in plants is described. The polysaccharide degrading enzyme can be used for a variety of applications, including in ethanol production. Use of the crop plant as the source of enzyme to obtain fermentable sugars, that can in turn be used in ethanol production is described. Transgenic plants expressing commercial levels of recombinant cellulases in plants on a reliable basis is shown. Expression vectors are engineered to provide for preferential expression of the enzymes to particular organelles or secreted to the cell wall in the plant.

DESCRIPTION OF THE DRAWINGS

FIG. 2 shows a sequence for the E1 cellulase encoding gene (SEQ ID NO: 1).

FIG. 4A shows a sequence for a vacuole targeting sequence (SEQ ID NO: 2) and FIG. 4B shows the barley alpha amylase sequence used (SEQ ID NO: 3).

FIG. 6 shows a sequence for CBH I encoding gene (SEQ ID NO: 4).

FIG. 15 shows a barley alpha amylase signal sequence (SEQ ID NO: 5) in italics with the sequence encoding cel7D (also known as cbh1-4) from *Phanerochaete chrysosporium* (SEQ ID NO: 6).

FIG. 16 is the sequence of an extended globulin-1 promoter used in the experiments (SEQ ID NO: 7).

FIG. 18 is the sequence encoding cel5A from *Phanerochaete chrysosporium* (SEQ ID NO: 8 with the BAASS sequence of SEQ ID NO: 5 in italics and a KDEL (SEQ ID NO: 12) sequence (SEQ ID NO: 9) in bold).

FIG. 20 is the sequence encoding CBH I from *P. chrysosporium* C1 (SEQ ID NO: 10) with the BAASS signal sequence of SEQ ID NO: 5 in italics.

FIG. 22 is the sequence encoding EG5 (SEQ ID NO: 11) with the BAASS signal sequence in italics (SEQ ID NO: 5) and the KDEL (SEQ ID NO: 12) sequence of SEQ ID NO: 9, in bold.

DETAILED DESCRIPTION OF THE PREFERRED EMBODIMENTS

Figure 1:
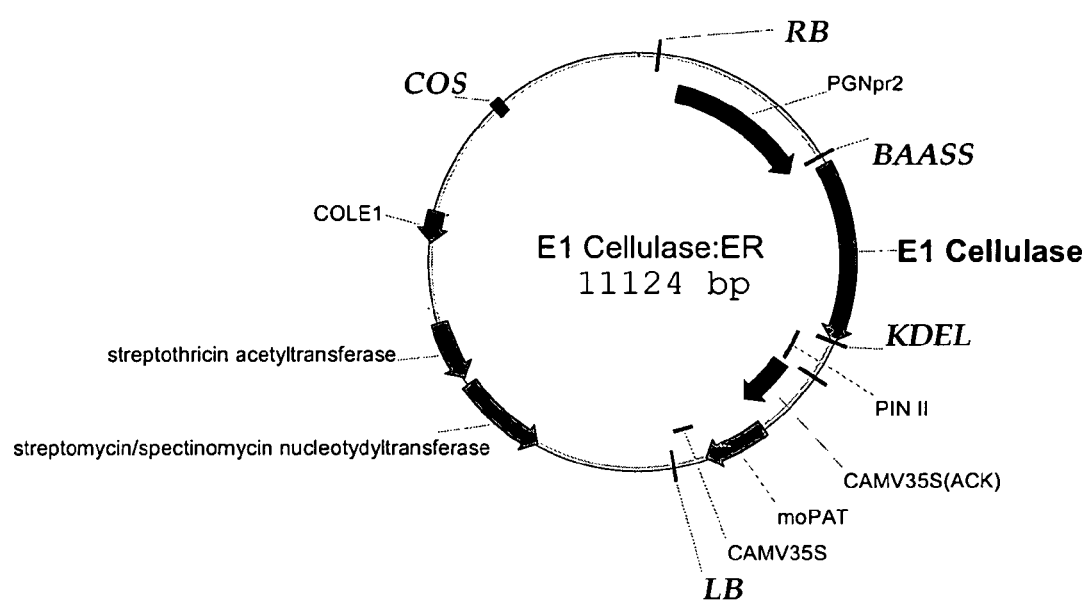
FIG. 1 is a construct map showing the construct for expressing E1 cellulase targeted to the endoplasmic reticulum (KDEL is disclosed as SEQ ID NO: 12).

The present invention is drawn to cost-effective methods for expressing polysaccharide degrading enzymes in plants and the use of same, particularly for the conversion of lignocellulosic biomass into ethanol. By "lignocellulosic biomass" is intended biomass that is comprised predominantly of plant cell walls and the components therein including, but not limited to, cellulose, hemicellulose, pectin, and lignin. Current methods for the production of ethanol, which utilize starch derived from corn grain, is a use of a food product for a fuel, and needs to be more cost effective.

The methods of the invention involve the use of lignocellulosic biomass that is currently under utilized for the production of ethanol. Such lignocellulosic biomass includes, for example, crop plant residues or other undesired plant material that may be left behind in the field after harvest or separated from the desired plant material. A crop refers to a collection of plants grown in a particular cycle. By "desired plant material" is intended the plant product that is the primary reason for commercially growing the plant. Such desired plant material can be any plant or plant part or plant product that has commercial value. Corn is grown for human and animal consumption, as well as to produce products such as industrial oils, fertilizer and many other uses. Soybeans and wheat are used primarily in food products. There are multitudes of purposes for which these plant materials can be utilized. The desired plant material also includes protein produced by a transgenic polynucleotide. In short, the desired plant material refers to any product from the plant that is useful. The invention allows for profitable use of what would otherwise be low value or waste material after the desired plant is obtained. In the invention, the enzyme used to degrade polysaccharides in a crop can be produced by the very crop that will be degraded, thereby providing clear advantages in eliminating or reducing the need for an outside source of the enzyme, compacting costs with its production by combining it with production of the cellulose source.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses.

The plant tissue used may be that of the original plant transformed with the enzyme, or can be a descendant obtained by crossing with the same plant or another plant, as described in the methods below.

While such lignocellulosic biomass contains vast amounts of polysaccharides, these polysaccharides are not readily fermentable into ethanol. These polysaccharides are constituents of plant cell walls and include, but are not limited to, cellulose, hemicellulose, and pectin. The present invention provides cost-effective methods that involve converting at least a portion of these polysaccharides, particularly the portion comprising cellulose, into a form that can be readily fermented into ethanol by the microorganisms that are presently used for ethanol production, namely yeasts and bacteria. The invention integrates the economical production of the enzymes required for the conversion of the polysaccharides in lignocellulosic biomass to ethanol with the production of the desired plant material and the simultaneous recovery of the desired material, the lignocellulosic raw material and the polysaccharide-degrading enzymes in a single harvest operation.

The methods of the invention involve the conversion of plant cell wall polysaccharides to fermentable sugars that can then be used in the production of ethanol or other desired molecules via fermentation methods known in the art. The use of the term "fermentable sugars" includes, but is not limited to, monosaccharides and disaccharides and also encompasses sugar derivatives such as, for example, sugar alcohols, sugar acids, amino sugars, and the like. The fermentable sugars of the invention encompass any sugar or sugar derivative that is capable of being fermented into ethanol via fermentation methods known in the art. In addition, one skilled in the art can appreciate that the enzymes expressed in plants of the invention may be used in any commercial polysaccharide-degrading process, such as in providing additives to animal feed (See, for example Rode et al., "Fibrolytic enzyme supplements for dairy cows in early lactation" *J. Dairy Sci.* 1999 October; 82(1):2121-6); industrial applications, (for example, in detergent applications, see Winetzky, U.S. Pat. No. 6,565,6131; in biofinishing of denims, see Vollmond, WO 97/25468); treatment of genes, or, in a preferred embodiment, in the production of ethanol.

To convert the cell wall polysaccharides to fermentable sugars, the methods of the invention involve producing in plant tissues one or more enzymes that are capable of degrading plant cell wall polysaccharides. Preferably, such enzymes are produced at high levels. Such enzymes and the sequences encoding them are known in the art.

Current sources of cell wall polysaccharide-degrading enzymes are fungal and microbial cultures. Producing high levels of cell wall polysaccharide-degrading enzymes in plants, particularly in grain crops, is less expensive and thus lowers the total cost of producing ethanol from lignocellulosic biomass (Z. Nikolov and D. Hammes. 2002. "Production of Recombinant Proteins from Transgenic Crops" in *Plants as Factories for Protein Production.*, E. E. Hood and J. A. Howard, Eds., Kluwer Academic Publishers, Dordrecht, the Netherlands pp. 159-174).

The methods of the invention involve transforming a plant with at least one nucleotide construct comprising at least one nucleotide sequence encoding an enzyme that is capable of degrading plant cell wall polysaccharides. The nucleotide sequence is operably linked to a promoter that drives expression in a plant. Preferably, the promoter will preferentially direct expression to a particular plant tissue. More preferably, the promoter will provide high-level expression in a particular plant tissue. The plant tissue in which the enzyme is expressed can include any plant tissue, such as leaf, seed, root, stem, tassel, anther, pollen, ovules, or any other tissue of the plant. In an embodiment the tissue is leaf. Most preferably, the promoter will provide high-level expression in a seed, or in a particular part of the seed, such as, for example, the embryo (sometimes referred to as the "germ"), endosperm, seed coat, bran or hull. Expression of 0.1% total soluble protein is necessary to provide economically practical expression. By "high-level expression" is intended that an enzyme of the invention is present in the plant tissue at a level of at least about 0.1% dry weight, or about 10% total soluble protein.

The methods can involve, one, two, three, four, five, or more of such enzymes. The enzymes are preferably produced in plant seeds, or in a particular portion thereof, such as, for example, in the embryo, endosperm, seed coat, bran or hull.

In one embodiment of the invention, the methods involve one or more cell wall polysaccharide-degrading enzymes. By cell wall "polysaccharide-degrading enzyme" is intended any enzyme that can be utilized to promote the degradation of the plant cell wall polysaccharides into fermentable sugars. While the methods of the invention encompass the production of one or more cell wall polysaccharide-degrading enzymes in a single plant, two or more enzymes can be produced in separate plants. For example, a first plant can be transformed with a first nucleotide construct comprising a first promoter operably linked to a first nucleotide sequence encoding a first polysaccharide-degrading enzyme. A second plant can also be transformed with a second nucleotide construct comprising a second promoter operably linked to a second nucleotide sequence encoding a second cell wall polysaccharide-degrading enzyme. The first and second enzymes can then be employed to degrade cell wall polysaccharides either in combination or sequentially.

Alternatively, the two or more enzymes can be produced in a single plant. The enzymes may be produced in the same tissue, expression directed to different tissue; expression may be directed to the same organelle or different organelles. For example, one enzyme may be expressed to the endoplasmic reticulum, and the same or a different enzyme expresssed to the vacuole. The result provides both various options for expression of more than one enzyme, for ease in use, and/or an increase in expression of the enzymes. This can be accomplished by any means known in the art for breeding plants such as, for example, cross pollination of the first and second plants that are described above and selection for plants from subsequent generations which express both the first and second enzymes. The plant breeding methods used herein are well known to one skilled in the art. For a discussion of plant breeding techniques, see Poehlman (1987) Breeding Field Crops. AVI Publication Co., Westport Conn. Many crop plants useful in this method are bred through techniques that take advantage of the plant's method of pollination. A plant is self-pollinating if pollen from one flower is transferred to the same or another flower of the same plant. A plant is cross-pollinated if the pollen comes from a flower on a different plant. For example, in *Brassica*, the plant is normally self sterile and can only be cross-pollinated unless, through discovery of a mutant or through genetic intervention, self compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (Zea mays L.) can be bred by both self-pollination and cross-pollination techniques. Maize has male flowers, located on the tassel, and female flowers, located on the ear, on the same plant. It can self or cross pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods that make one plant pool male sterile, and the other the male fertile pollen donor. This can be accomplished by hand detasseling, cytoplasmic male sterility, or control of male sterility through a variety of methods well known to the skilled breeder. Examples of more sophisticated male sterility systems include those described at Brar et al., U.S. Pat. Nos. 4,654,465 and 4,727,219 and Albertsen et al. U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as "Plant Breeding Methodology" edit. Neal Jensen, John Wiley & Sons, Inc. (1988). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

A single plant can also be transformed with both the first and second nucleotide constructs described above or with a single nucleotide construct comprising the first promoter operably linked to the first nucleotide sequence and the second promoter operably linked to the second nucleotide sequence. Furthermore, it is recognized that both the first and second promoters can be the same or different depending on whether or not it is desired to express the first and second enzymes at the same level, time, and/or tissue in a plant or in separate plants.

Furthermore, as noted, the plant can be also transformed using such methods with another nucleotide sequence which creates a desired plant product. Such product can provide the plant with increased value, where the expression provides insect resistance, disease resistance, herbicide resistance, increased yield, increased tolerance to environmental stress, increased or decreased starch, oil or protein content, for example. The protein expressed in the plant can also be the desired plant product itself. By way of example, but not limitation such products can include production of proteases in plants (See U.S. Pat. No. 6,087,558); production of aprotinin in plants (U.S. Pat. No. 5,824,870); production of avidin in plants (U.S. Pat. No 5,767,379); production of viral vaccines in plants (U.S. Pat. No. 6,136,320); production of transmissible gastroenteritis and hepatitis vaccines in plants (U.S. Pat. Nos. 5,914,123 and 6,034,298).

The enzymes of the invention encompass enzymes that can be employed to degrade plant cell wall polysaccharides into fermentable sugars. Such enzymes are known in the art and include, but are not limited to, enzymes that can catalyze the degradation of cellulose, hemicellulose, and/or pectin. In particular, the methods of the invention are drawn to cellulose-degrading enzymes. By "cellulose-degrading enzyme" is intended any enzyme that can be utilized to promote the degradation of cellulose into fermentable sugars including, but not limited to, cellulases and glucosidases. By way of example, without limitation, the enzymes classified in Enzyme Classification as 3.2.1.x are included within the scope of the invention. An example of the many enzymes which may be employed in the invention is presented in Table 2, a list of enzymes in the category by the Nomenclature Committee of the International Union of Biochemistry and Molecular Biology (NC-IUBMB).

TABLE 2

Polysaccharide degrading enzymes

EC 3.2.1.1 α-amylase
EC 3.2.1.2 β-amylase
EC 3.2.1.3 glucan 1,4-α-glucosidase
EC 3.2.1.4 cellulase
EC 3.2.1.6 endo-1,3(4)-β-glucanase
EC 3.2.1.7 inulinase
EC 3.2.1.8 endo-1,4-p-xylanase
EC 3.2.1.10 oligo-1,6-glucosidase
EC 3.2.1.11 dextranase
EC 3.2.1.14 chitinase
EC 3.2.1.15 polygalacturonase
EC 3.2.1.17 lysozyme
EC 3.2.1.18 exo-α-sialidase
EC 3.2.1.20 α-glucosidase
EC 3.2.1.21 β-glucosidase
EC 3.2.1.22 α-galactosidase
EC 3.2.1.23 β-galactosidase
EC 3.2.1.24 α-mannosidase
EC 3.2.1.25 β-mannosidase
EC 3.2.1.26 β-fructofuranosidase
EC 3.2.1.28 αα-trehalase
EC 3.2.1.31 β-glucuronidase
EC 3.2.1.32 xylan endo-1,3-β-xylosidase
EC 3.2.1.33 amylo-1,6-glucosidase
EC 3.2.1.35 hyaluronoglucosaminidase
EC 3.2.1.36 hyaluronoglucuronidase
EC 3.2.1.37 xylan 1,4-β-xylosidase
EC 3.2.1.38 β-D-fucosidase
EC 3.2.1.39 glucan endo-1,3-β-D-glucosidase
EC 3.2.1.40 β-L-rhamnosidase
EC 3.2.1.41 pullulanase
EC 3.2.1.42 GDP-glucosidase
EC 3.2.1.43 β-L-rhamnosidase
EC 3.2.1.44 fucoidanase
EC 3.2.1.45 glucosylceramidase
EC 3.2.1.46 galactosylceramidase
EC 3.2.1.47 galactosylgalactosylglucosylceramidase
EC 3.2.1.48 sucrose β-glucosidase
EC 3.2.1.49 α-N-acetylgalactosaminidase
EC 3.2.1.50 α-N-acetylglucosaminidase
EC 3.2.1.51 α-L-fucosidase
EC 3.2.1.52 β-L-N-acetylhexosaminidase
EC 3.2.1.53 β-N-acetylgalactosaminidase
EC 3.2.1.54 cyclomaltodextrinase
EC 3.2.1.55 α-N-arabinofuranosidase
EC 3.2.1.56 glucuronosyl-disulfoglucosamine glucuronidase
EC 3.2.1.57 isopullulanase
EC 3.2.1.58 glucan 1,3-β-glucosidase
EC 3.2.1.59 glucan endo-1,3-α-glucosidase
EC 3.2.1.60 glucan 1,4-α-maltotetraohydrolase
EC 3.2.1.61 mycodextranase
EC 3.2.1.62 glycosylceramidase
EC 3.2.1.63 1,2-α-L-fucosidase
EC 3.2.1.64 2,6-β-fructan 6-levanbiohydrolase
EC 3.2.1.65 levanase TABLE 2-continued Polysaccharide degrading enzymes EC 3.2.1.66 quercitrinase
EC 3.2.1.67 galacturan 1,4-α-galacturonidase
EC 3.2.1.68 isoamylase
EC 3.2.1.70 glucan 1,6-α-glucosidase
EC 3.2.1.71 glucan endo-1,2-β-glucosidase
EC 3.2.1.72 xylan 1,3-β-xylosidase
EC 3.2.1.73 licheninase
EC 3.2.1.74 glucan 1,4-β-glucosidase
EC 3.2.1.75 glucan endo-1,6-β-glucosidase
EC 3.2.1.76 L-iduronidase
EC 3.2.1.77 mannan 1,2-(1,3)-α-mannosidase
EC 3.2.1.78 mannan endo-1,4-β-mannosidase
EC 3.2.1.80 fructan β-fructosidase
EC 3.2.1.81 agarase
EC 3.2.1.82 exo-poly-α-galacturonosidase
EC 3.2.1.83 κ-carrageenase
EC 3.2.1.84 glucan 1,3-β-glucosidase
EC 3.2.1.85 6-phospho-β-galactosidase
EC 3.2.1.86 6-phospho-β-glucosidase
EC 3.2.1.87 capsular-polysaccharide endo-1,3-α-galactosidase
EC 3.2.1.88 β-L-arabinosidase
EC 3.2.1.89 arabinogalactan endo-1,4-β-galactosidase
EC 3.2.1.91 cellulose 1,4-β-cellobiosidase
EC 3.2.1.92 peptidoglycan β-N-acetylmuramidase
EC 3.2.1.93 αα-phosphotrehalase
EC 3.2.1.94 glucan 1,6-α-isomaltosidase
EC 3.2.1.95 dextran 1,6-α-isomaltotriosidase
EC 3.2.1.96 mannosyl-glycoprotein endo-β-N-acetylglucosaminidase
EC 3.2.1.97 glycopeptide α-N-acetylgalactosaminidase
EC 3.2.1.98 glucan 1,4-α-maltohexaosidase
EC 3.2.1.99 arabinan endo-1,5-α-L-arabinosidase
EC 3.2.1.100 mannan 1,4-mannobiosidase
EC 3.2.1.101 mannan endo-1,6-α-mannosidase
EC 3.2.1.102 blood-group-substance endo-1,4-β-galactosidase
EC 3.2.1.103 keratan-sulfate endo-1,4-β-galactosidase
EC 3.2.1.104 steryl-β-glucosidase
EC 3.2.1.105 strictosidine β-glucosidase
EC 3.2.1.106 mannosyl-oligosaccharide glucosidase
EC 3.2.1.107 protein-glucosylgalactosylhydroxylysine glucosidase
EC 3.2.1.108 lactase
EC 3.2.1.109 endogalactosaminidase
EC 3.2.1.110 mucinaminylserine mucinaminidase
EC 3.2.1.111 1,3-α-L-fucosidase
EC 3.2.1.112 2-deoxyglucosidase
EC 3.2.1.113 mannosyl-oligosaccharide 1,2-α-mannosidase
EC 3.2.1.114 mannosyl-oligosaccharide 1,3-1,6-α-mannosidase
EC 3.2.1.115 branched-dextran exo-1,2-α-glucosidase
EC 3.2.1.116 glucan 1,4-α-maltotriohydrolase
EC 3.2.1.117 amygdalin β-glucosidase
EC 3.2.1.118 prunasin β-glucosidase
EC 3.2.1.119 vicianin β-glucosidase
EC 3.2.1.120 oligoxyloglucan β-glycosidase
EC 3.2.1.121 polymannuronate hydrolase
EC 3.2.1.122 maltose-6'-phosphate glucosidase
EC 3.2.1.123 endoglycosylceramidase
EC 3.2.1.124 3-deoxy-2-octulosonidase
EC 3.2.1.125 raucaffricine β-glucosidase
EC 3.2.1.126 coniferin β-glucosidase
EC 3.2.1.127 1,6-α-L-fucosidase
EC 3.2.1.128 glycyrrhizinate β-glucuronidase
EC 3.2.1.129 endo-α-sialidase
EC 3.2.1.130 glycoprotein endo-α-1,2-mannosidase
EC 3.2.1.131 xylan α-1,2-glucuronosidase
EC 3.2.1.132 chitosanase
EC 3.2.1.133 glucan 1,4-α-maltohydrolase
EC 3.2.1.134 difructose-anhydride synthase
EC 3.2.1.135 neopullulanase
EC 3.2.1.136 glucuronoarabinoxylan endo-1,4-β-xylanase
EC 3.2.1.137 mannan exo-1,2-1,6-β-mannosidase
EC 3.2.1.139 α-glucuronidase
EC 3.2.1.140 lacto-N-biosidase
EC 3.2.1.141 4-α-D-{(1→4)-α-D-glucano}trehalose trehalohydrolase
EC 3.2.1.142 limit dextrinase
EC 3.2.1.143 poly(ADP-ribose) glycohydrolase
EC 3.2.1.144 3-deoxyoctulosonase
EC 3.2.1.145 galactan 1,3-β-galactosidase
EC 3.2.1.146 β-galactofuranosidase
EC 3.2.1.147 thioglucosidase TABLE 2-continued Polysaccharide degrading enzymes EC 3.2.1.149 β-primeverosidase
EC 3.2.1.150 oligoxyloglucan reducing-end-specific cellobiohydrolase
EC 3.2.1.151 xyloglucan-specific endo-β-1,4-glucanase
EC 3.2.1.152 mannosylglycoprotein endo-β-mannosidase
EC 3.2.1.153 fructan β-(2,1)-fructosidase
EC 3.2.1.154 fructan β-(2,6)-fructosidase
EC 3.2.1.156 oligosaccharide reducing-end xylanase For the degradation of cellulose, for example, two general types of cellulase enzymes can be employed. Cellulase enzymes which cleave the cellulose chain internally are referred to as endo-β-1,4-glucanases (E.C. 3.2.1.4) and serve to provide new reducing and non-reducing chain termini on which exo-β-1,4-glucanases (cellobiohydrolase, CBH; E.C. 3.2.1.91) can operate (Tomme et al. (1995) *Microbial Physiology* 37:1-81). Two types of exoglucanase have been described that differ in their approach to the cellulose chain. One type attacks the non-reducing end and the other attacks the reducing end. The product of the exoglucanase reaction is typically cellobiose, so a third activity, β-D-glucosidase (E.C. 3.2.1.21), is required to cleave cellobiose to glucose. The exoglucanase can also yield longer glucose chains (up to 6 glucose units) that will require a β-D-glucosidase activity to reduce their size. Relative to the other enzyme activities needed for degradation of cellulose into fermentable sugars, only a minor amount of the β-D-glucosidase activity is required. Therefore, while the methods of the invention encompass the production of such a glucosidase in a plant, the necessary glucosidase activity could be supplied by a downstream fermentative organism or from β-D-glucosidase enzyme that is added during saccharification and/or fermentation.

Nucleotide sequences encoding endo-β-1,4-glucanases, exo-β-1,4-glucanases, and β-D-glucosidases are known in the art. Nucleotide sequences encoding endo-β-1,4-glucanases include, but are not limited to, the nucleotide sequence having Accession No. U33212. Nucleotide sequences encoding exo-β-1,4-glucanases include, but are not limited to, the nucleotide sequence having Accession No. X69976. Nucleotide sequences encoding β-D-glucosidases include, but are not limited to, the nucleotide sequence having Accession No. U13672.

Expression of cellulases in plants has several advantages. Plants are more economical to grow and can be far more readily produced in large quantities than fungi. In addition, recombinant protein targeted to seeds allows for stable storage of the recombinant proteins for extended periods. The inventors have determined that expression of cellulases in plants at commercial levels on a reliable basis is feasible and provides substantial advantages over prior attempts of producing the enzyme in microorganisms.

One reason that cellulose utilization has not yet been commercially realized is due to the high cost of the large quantities of cellulase enzymes required for its complete hydrolysis. Approximately 1.3 million tons/yr of cellulase would be required to convert the 48 million tons of stover-derived cellulose to glucose. While the development of superior enzymes for processing of plant polymers is important, superior enzymes are of little value unless the means to produce them economically on a large scale are also available. The methods of the instant invention provide for the cost-effective production of cellulases and other polysaccharide-degrading enzymes in plants, particularly transgenic maize.

The inventors have discovered that it is possible to obtain commercial level expression of a recombinant nucleic acid sequence encoding cellulases in plants, with improved enzyme production when expression is directed to the seed of the plant, to particular organelles and/or cell wall, and that expression is possible and preferable in corn. The result is consistent, reliable production in plants of commercial levels of cellulases.

With today's specific activity, 1.2 million tons of cellulase are required to convert 48 million tons of cellulose (from 120 million tons of corn stover) to a sugar stream. This would require 120 million tons of grain assuming the enzymes showing synergy in cellulose digestion were present at expression levels of 1% of dry weight of seed. US production of corn grain is estimated at 200 MM tons per year. Therefore at these expression levels, 60% of corn production would be required for the cellulase enzymes. However, with improved enzymes and expression technology, a much lower amount of the corn crop would be required to produce enough enzymes to convert all the available cellulose in corn stover to glucose. While Ziegler, supra, showed high expression levels in *Arabidopsis*, the plant is impractical for reliable commercial production of the enzymes. The expression levels in both Ziegler and Dai, supra, is several orders of magnitude below commercially practical levels.

Further, expression of cellulases in corn has been demonstrated for the first time. Corn has considerable advantages over other plants as bioreactors. In comparison with other plants, it produces seed which is easily stored and transported, has low production costs, the plant parts have use in a variety of processes and products, thereby reducing costs by the sale of coproducts, and it is the largest crop in North America in terms of both acreage and total value. Thus production of the enzymes in corn is desirable.

Further, according to the present invention, the preferential direction of expression of the cellulases to internal organelles and/or cell wall of the plant is a preferred method of expressing the enzymes at high levels. The inventors have determined that targeting the expression of E1 endo-1,4-β-D-glucanase (E1 cellulase) to the cell wall results in expression levels of more than 1% total soluble protein, and when targeted to the endoplasmic reticulum (ER) results in levels of expression over 15% of the total soluble protein (TSP) using extraction methods as described in Example 3. High levels of expression were also achieved when the enzyme was targeted to the vacuole. In this instance, seeds had levels of expression in excess of 10% TSP. When cellobiohydrolase I (CBH I) was targeted to the cell wall, high levels of expression were obtained, and improved expression, (in excess of 15% TSP) was obtained when targeted to the ER. However, vacuole expression resulted in no expression for CBH I. Thus, targeting to either the cell wall or specific organelles can improve expression. As discussed supra, more than one enzyme can be expressed in crop plants. For example, the E1 cellulase expression can be preferentially directed to the endoplasmic reticulum, to the vacuole, or cell wall, and CBH I targeted to the cell wall or to the endoplasmic reticulum, the person skilled in the art selecting the targeted tissue so that the each enzyme expresses at optimum levels, and both enzymes available in one plant or one crop.

In addition to cellulose-degrading enzymes, enzymes that degrade hemicellulose and pectin can also be employed in the methods of the invention. While it is recognized that the soluble sugars can be liberated from the hemicellulose portion of lignocellulosic biomass by incubation in dilute acid at high temperatures, enzymes can be also employed in the methods of the instant invention to convert hemicellulose into fermentable sugars. Such enzymes that can be used to the convert the polysaccharides of the hemicellulose portion into fermentable sugars are known in the art and include, but are not limited to, endo-β-1,4-xylanases, endo-β-1,4-mannanases, endo-β-1,4-galactanases, endoxylanases, α-glucuronidases, α-arabinofuranosidases, and α-arabinosidases. Nucleotide sequences encoding such enzymes are also known in the art. See http://us.expasy.org/cgi-bin/lists?glycosid.txt. Furthermore, additional fermentable sugars can be liberated from the pectin portion via the use of enzymes such as, for example, pectinases. Nucleotide sequences encoding such enzymes are also known in the art. See, Fry, S. C. 1985. Primary cell wall metabolism. Oxford Surveys of Plant Molecular and Cell Biology, ed. B. J. Miflin. 2:1-42. Oxford: Clarendon.

In accordance with the present invention, a DNA molecule comprising a transformation/expression vector is engineered to incorporate a polysaccharide degrading—encoding cDNA. Such enzymes can then be used in any process employing polysaccharide degrading enzymes, such as in feed additivies, treatment of genes, or ethanol production. In one embodiment of the invention, when cellulase enzymes are used in ethanol production, it is preferable to use the following criteria to select the cellulases for expression in plants. Such enzymes will be those stable at temperatures and at a pH that is higher or lower than the temperature or pH at which the plant expressing the enzyme grows, thereby reducing the possiblity the enzyme will have an adverse impact on the plant cell. Further, when selecting more than one enzyme for expression in a plant the pH and temperature stability requirements of the enzymes will be such that one enzyme does not require an environment hostile to the other enzyme in order to remain stable. It is also preferable that the enzymes when combined in the polysaccharide degrading process have a synergistic effect on the substrate. In one embodiment these cellulase enzymes are thermostable to at least 45° C., have pH optima that are similar, exhibit synergistic activity on lignocellulosic substrates, and the genes encoding these enzymes have been cloned.

Using these criteria, in one embodiment, the E1 β-1,4-endoglucanase from *Acidothermus cellulolyticus* (Mohagheghi et al. (1986) Isolation and Characterization of *Acidothermus cellulolyticus* gen. Nov., sp. Nov., a new genus of thermophillic, acidophillic, cellulolytic bacteria. *Int. J. Syst. Bacteriol.* 36:435-443; Nieves et al. (1995) *Appl. Biochem. Biotechnol.* 51/52:211-223; U.S. Pat. No. 5,536,655), cellobiohydrolase I (CBH I) from *Trichoderma reesii* (Shoemaker et al. (1983). Molecular Cloning of Exo-Cellobiohydrolase I Derived From *Trichoderma Reesei* Strain L27. *Bio/Technology* 691-696) and the β-D-glucosidase from *Candida wickerhamii* (Skory and Freer (1995) *Appl. Environ. Microbiol.* 61:518-525; Freer (1993) *J. Biol. Chem.* 268:9337-9342) have been selected. This latter enzyme is a preferred glucosidase because it is resistant to feedback inhibition by glucose and cellobiose—an important consideration if one separates the process of saccharification from fermentation. If saccharification is performed separately from fermentation, the glucosidase should be selected which will not be feedback inhibited by their products. The first two enzymes—E1 and CBHI—have been shown to exhibit synergistic activity on lignocellulosic substrates that have been pretreated with dilute acid and steam (Baker et al. (1994) *Appl. Biochem. Biotechnol.* 45/46:245-256). E1 has optimal activity at 81° C. (Table 3) but is compatible at 45-50° C. with the CBHI enzyme which shows optimal and sustained activity at 50° C. Thermostable enzymes with high temperature optima are less likely to produce detrimental affects on plants during their growth and development at ambient temperatures. Some physical characteristics of the selected enzymes for this embodiment of the invention are presented in Table 3.

TABLE 3

Characteristics of Selected Cellulose-Degrading Enzymes

| | E1 cellulase | CBH I | β-glucosidase |
|---|---|---|---|
| Family | 5-3.2.1.4 | 7-3.2.1.91 | 1-3.2.1.21 |
| Calculated MW | 521 aa; 56,500 Da | 496 aa; 52,500 Da | 94,000 Da native 116,000 Da in yeast |
| Native source | Bacterial | Fungal | Fungal |
| (catalytic domain) | 363 aa; 40,610 Da | | |
| MW by SDS PAGE | 72,000 Da | 65,000 Da | 94,000 Da |
| (catalytic domain) | 60,000 Da | | 72,000 non-glycosyl |
| Glycosylated native protein | No | Yes, primarily linker region | Yes, 30% |
| pI | 5.2 (holo) 4.87 (cat domain) | 4.51 | 3.89[2] |
| pH optimum | 5–6 | 5 | 4.75 |
| Temperature optimum | 81° C. | 45–50° C. | <45° C. |
| Bond cleaved | β-1,4-glycosidic | β-1,4-glycosidic | β1,4-glycosidic |
| Mechanism | Retained anomeric configuration[1] | Retained anomeric configuration[1] | Retained anomeric configuration[1] |
| Substrates | Cellulose fibrils; purified cellulose preparations (Solka-floc, Sigmacell, Avicel); para-nitrophenyl-β-1,4-D-cellobiose (pNPC); methyl-umbelliferyl-β-1,4-D-cellobioside (MUC) | Cellulose fibrils; purified cellulose preparations (Solka-floc, Sigmacell, Avicel) | Cellobiose (and other water-soluble cello-oligomers up to dp 6); other β-1,4-glycosides (para-nitrophenyl-β-1,4-D-glucose (pNPG); methyl-umbelliferyl-β-1,4-D-glucose (MUG) |
| Primary reaction products | Decreased degree of polymerization (dp), long-chain, water-insoluble cellulose | Cellobiose (and other water-soluble short chain cello-oligomers) | Glucose |

[1]Schulein (2000) Biochim. Biophys. Acta 1543: 239–252.
[2]Freer (1993) J. Biol. Chem. 268: 9337–9342.

There are numerous cellulase genes cloned and sequenced from a wide variety of bacteria, fungi and plants. For example, see, Schulein M, 2000. Protein engineering of cellulases. *Biochim. Biophys. Acta* 1543:239-252; Tomme P, et al., 1995. Cellulose Hydrolysis by Bacteria and Fungi. *Advances in Microbial Physiology* 37:1-81; Zeigler et al, supra, Dai et al, supra, Ziegelhoffer, supra, Jensen supra; Henrissat B. A, Classification of glycosyl hydrolases based on amino-acid sequence similarities *Biochem. J.* 280:309-316(1991); Henrissat B., Bairoch A., New families in the classification of glycosyl hydrolases based on amino-acid sequence similarities, *Biochem. J* 293:781-788(1993); Henrissat B., Bairoch A. Updating the sequence-based classification of glycosyl hydrolases, *Biochem. J.* 316:695-696(1996); Davies G., Henrissat B, Structures and mechanisms of glycosyl hydrolases, *Structure* 3:853-859(1995); Jang. S. J. et al, New integration vector using a cellulase gene as a screening marker for *Lactobacillus*, *FEMS Microbiol Lett*. 2003 Jul. 29; 224(2):191-5; Rees, H. C. et al. Detecting cellulase and esterase enzyme activities encoded by novel genes present in environmental DNA libraries. Extremophiles. Jul. 5, 2003; Moriya, T. et al. Cloning and overexpression of the avi2 gene encoding a major cellulase produced by *Humicola insolens* FERM BP-5977. *Biosci Biotechnol Biochem*. 2003 June; 67(6): 1434-7; Sanchez, M M et al., Exo-mode of action of cellobiohydrolase Cel48C from *Paenibacillus* sp. BP-23. A unique type of cellulase among Bacillales. *Eur J Biochem*. 2003 July;270(13):2913-9; Abdeev, R. M. et al, Expression of a thermostable bacterial cellulase in transgenic tobacco plants *Genetika*. 2003 March;39(3):376-82.; PMID: 12722638; Qin Q et al., Characterization of a tomato protein that inhibits a xyloglucan-specific endoglucanase. *Plant J.* 2003 May;34 (3):327-38.; Murray P. G. et al., Molecular cloning, transcriptional, and expression analysis of the first cellulase gene (cbh2), encoding cellobiohydrolase II, from the moderately thermophilic fungus *Talaromyces emersonii* and structure prediction of the gene product. *Biochem Biophys Res Commun*. 2003 Feb. 7; 301(2):280-6; Nakashima, K. I. et al., Cellulase genes from the parabasalian symbiont *Pseudotrichonympha grassii* in the hindgut of the wood-feeding termite *Coptotermes formosanus*. *Cell Mol Life Sci*. 2002 September; 59(9):1554-60. The above is a small sampling of the myriad of cellulase encoding genes available to one skilled in the art.

The use of the term "nucleotide constructs" and "nucleic acids" herein is not intended to limit the present invention to nucleotide constructs comprising DNA. Those of ordinary skill in the art will recognize that nucleic acid molecules, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like. By referring to a "heterologous" nucleic acid is meant that the nucleic acid has been introduced in to the plant by human intervention, such as by transformation with a nucleotide sequence, crossing or backcrossing with another plant transformed with the nucleotide sequence, infection of the plant through bacterial or viral methodology, or the like.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990). When targeting the enzyme to the cell wall use of a signal sequence is necessary. One example is the barley alpha-amylase signal sequence (Rogers, J. C. 1985. Two barley alpha-amylase gene families are regulated differently in aleurone cells. *J. Biol. Chem.* 260: 3731-3738).

In a preferred embodiment, the enzyme production is retained in the endoplasmic reticulum of the plant cell. This may be accomplished by use of a localization sequence, such as KDEL (SEQ ID NO: 12). This sequence (Lys-Asp-Glu-Leu) (SEQ ID NO: 12) contains the binding site for a receptor in the endoplasmic reticulum. (Munro, S. and Pelham, H. R. B. 1987 "A C-terminal signal prevents secretion of luminal ER proteins" *Cell* 48:899-907. The use of such a localization sequence will increase expression over levels obtained when the enzyme is otherwise expressed in the cytoplasm.

Targeting the enzyme to the vacuole is another preferred embodiment. Signal sequences to accomplish this are well known. For example, Raikhel U.S. Pat. No. 5,360,726 shows a vacuole signal sequence as does Warren et al at U.S. Pat. No. 5,889,174. Vacuolar targeting signals may be present either at the amino-terminal portion, (Holwerda et al., *The Plant Cell*, 4:307-318 (1992), Nakamura et al., *Plant Physiol.*, 101:1-5 (1993)), carboxy-terminal portion, or in the internal sequence of the targeted protein. (Tague et al., *The Plant Cell*, 4:307-318 (1992), Saalbach et al. *The Plant Cell*, 3:695-708 (1991)). Additionally, amino-terminal sequences in conjunction with carboxy-terminal sequences are responsible for vacuolar targeting of gene products (Shinshi et al. *Plant Molec. Biol.* 14:357-368 (1990)).

The nucleotide constructs of the invention encompass expression cassettes for expression in the plant of interest. The cassette will include 5' and 3' regulatory sequences operably linked to a nucleotide sequence encoding a polysaccharide-degrading enzyme of the invention. By "operably linked" is intended a functional linkage between a promoter and a second sequence, wherein the promoter sequence initiates and mediates transcription of the nucleotide sequence corresponding to the second sequence. Generally, operably linked means that the nucleotide sequences being linked are contiguous and, where necessary to join two protein coding regions, contiguous and in the same reading frame. Promoter elements employed to control expression of cellulases and the selection gene, respectively, can be any plant-compatible promoter.

In the methods of the invention, a number of promoters that direct expression of a gene in a plant can be employed. Such promoters can be selected from constitutive, chemically-regulated, inducible, and tissue-preferred promoters. Constitutive promoters include, for example, the core CaMV 35S promoter (Odell et al. (1985) *Nature* 313:810-812); ubiquitin promoters (Quail et al., 5,510,474; ubiquitin-like promoters (Jilka et al. U.S. Publication 20030066108); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730), and the like. Other constitutive promoters include, for example, those described at U.S. Pat. Nos. 5,608,149; 5,608,144; 5,604,121; 5,569,597; 5,466,785; 5,399,680; 5,268,463; and 5,608,142.

Chemically-regulated promoters can be used to modulate the expression of a gene in a plant through the application of an exogenous chemical regulator. Chemically-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

In an embodiment of the invention the promoter is a seed-preferred promoter that is active during seed development. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters of particular interest are those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. *Plant J.* 4: 567-577), the P-gene promoter from corn (Chopra et al. 1996. Alleles of the maize P gene with distinct tissue specificities encode Myb-homologous proteins with C-terminal replacements. Plant Cell 7:1149-1158, Erratum in *Plant Cell*. 1997, 1:109), the globulin-1 promoter from corn (Belanger and Kriz. 1991. Molecular basis for Allelic Polymorphism of the maize Globulin-1 gene. *Genetics* 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase$_{1-2}$ Gene Capable of Conferring Tissue-Specific Gene Expression in Transgenic Maize. *Plant Science* 163:865-872); Genbank accession number AF359511.

In a preferred embodiment, the globulin promoter (PGNpr2) is used. This is the promoter of the maize globulin-1 gene, described by Belanger, F. C. and Kriz, A. L. 1991. Molecular Basis for Allelic Polymorphism of the maize Globulin-1 gene. *Genetics* 129: 863-972. It also can be found as accession number L22344 in the Genbank database. Another example is the phaseolin promoter. See, Bustos et al. 1989. Regulation of B-glucuronidase expression in transgenic tobacco plants by an A/T-rich cis-acting sequence found upstream of a french bean B-phaseolin gene. *The Plant Cell*. (1): 839-853.

In a preferred embodiment, the expression vector also contains a gene encoding a selection marker that is functionally linked to a promoter that controls transcription initiation. For a general description of plant expression vectors and reporter genes, see Gruber et al. 1993. "Vectors for Plant Transformation" in Methods of Plant Molecular Biology and Biotechnology. CRC Press. p 89-119. In a preferred embodiment, the selective gene is a glufosinate-resistance encoding DNA and in another preferred embodiment can be the phosphinothricin acetyl transferase ("PAT") or maize optimized PAT gene under the control of the CaMV 35S promoter. The gene confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

In addition to a promoter, the expression cassette can include one or more enhancers. By "enhancer" is intended a cis-acting sequence that increases the utilization of a promoter. Such enhancers can be native to a gene or from a heterologous gene. Further, it is recognized that some promoters can contain one or more native, enhancers or enhancer-like elements.

The termination region can be native with the transcriptional initiation region, can be native with the operably linked DNA sequence of interest, or can be derived from another source. Convenient termination regions are available from the Ti-plasmid of *A. tumefaciens*, such as the octopine synthase and nopaline synthase termination regions. In one embodiment of the invention the pin II terminator from the protease inhibitor II gene from potato (An et al., 1989. Functional analysis of the 3' control region of the potato wound-inducible proteinase inhibitor II gene. *Plant Cell* 1: 115-122) is used. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477-498.

Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes can additionally contain 5'-leader sequences in the expression cassette construct. Such leader sequences can act to enhance translation. Translation leaders are known in the art and include but are not limited to: picornavirus leaders, for example, potyvirus leaders such as the TEV leader (Tobacco Etch Virus) (Allison et al. (1986); MDMV leader (Maize Dwarf Mosaic Virus); *Virology* 154: 9-20), untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Czech (Liss, New York), pp. 237-256); and maize chlorotic mottle virus leader (MCMV) (Lommel et al. (1991) *Virology* 81:382-385). Other methods known to enhance translation can also be utilized, for example, introns, and the like.

In preparing the nucleotide construct, the various DNA fragments can be manipulated, so as to provide for the DNA sequences in the proper orientation and, as appropriate, in the proper reading frame. Toward this end, adapters or linkers can be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Obviously, many variations on the promoters, selectable markers, signal sequences and other components of the construct are available to one skilled in the art.

The methods available for construction of recombinant genes comprising various modifications for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene is engineered to contain desired features, such as the desired localization sequences, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context will encode a polysaccharide degrading enzyme, such as E1 or CBH I; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In accordance with the present invention, a transgenic plant is produced that contains a DNA molecule, comprised of elements as described above, integrated into its genome so that the plant expresses a heterologous cellulase-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al. 1993. "Procedures for Introducing Foreign DNA into Plants" in *Methods in Plant Molecular Biology and Biotechnology*, Glick et al (eds) CRC Press pp. 67-68 and by Phillips et al. 1988 "Cell/Tissue Culture and In Vitro Manipulation" in *Corn and Corn Improvement* 3d Edit. Sprague et al (eds) American Soc. of Agronomy pp. 345-387. The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al. 1992. *Bio/Technology* 10:26; and Weisinger et al. 1988. *Ann. Rev. Genet.* 22: 421-477. For example, the DNA construct may be introduced into the genomic DNA of the plant cell using techniques such as microprojectile-mediated delivery (Klein et al. 1987. *Nature* 327: 70-73); electroporation (Fromm et al. 1985. *Proc. Natl. Acad. Sci.* 82: 5824); polyethylene glycol (PEG) precipitation (Paszkowski et al. 1984. *Embo J.* 3: 2717-272); direct gene transfer (WO 85/01856 and EP No. 0 275 069); in vitro protoplast transformation (U.S. Pat. No. 4,684,611) and microinjection of plant cell protoplasts or embryogenic callus (Crossway, 1985. *Mol. Gen. Genetics* 202:179-185). Co-cultivation of plant tissue with *Agrobacterium tumefaciens* is another option, where the DNA constructs are placed into a binary vector system (Ishida et al. 1996. "High Efficiency Transformation of Maize (*Zea mays* L.) Mediated by *Agrobacterium tumefaciens*". *Nature*

*Biotechnology* 14:745-750). The virulence functions of the *Agrobacterium tumefaciens* host will direct the insertion of the construct into the plant cell DNA when the cell is infected by the bacteria. See, for example Horsch et al. 1984. *Science* 233: 496-498, and Fraley et al. 1983. *Proc. Natl. Acad. Sci.* 80: 4803.

Standard methods for transformation of canola are described by Moloney et al. 1989. "High Efficiency Transformation of *Brassica napus* Using *Agrobacterium* Vectors" *Plant Cell Reports* 8:238-242. Corn transformation is described by Fromm et al, 1990. *BiolTechnology* 8:833 and Gordon-Kamm et al, supra. *Agrobacterium* is primarily used in dicots, but certain monocots such as maize can be transformed by *Agrobacterium*. U.S. Pat. No. 5,550,318. Rice transformation is described by Hiei et al. 1994. "Efficient Transformation of Rice (*Oryza sativs* L.) Mediated by *Agrobacterium* and Sequence Analysis of the Boundaries of the T-DNA" The Plant Journal 6(2): 271-282, Christou et al. 1992. *Trends in Biotechnology* 10:239 and Lee et al. 1991. *Proc. Nat'l Acad. Sci. USA* 88:6389. Wheat can be transformed by techniques similar to those used for transforming corn or rice. Sorghum transformation is described by Casas et al., 1997. Transgenic sorghum plants obtained after microprojectile bombardment of immature inflorescences. In vitro cellular and developmental biology, *Plant.* 33:92-100 and by Wan et al. 1994. *Plant Physiology.* 104:37. Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi-II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid.

Further, the Ishida protocol as described provides for growing fresh culture of the *Agrobacterium* on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than $OD600=0.5$ and is preferably between 0.2 and 0.5. The bacteria are then centrifuged to remove the media and resuspended in the co-culture medium. Since Hi-II is used, medium preferred for Hi-II is used. This medium is described in considerable detail by Armstrong, C. I. and Green C. E. 1985. Establishment and maintenance of friable, embryogenic maize callus and involvement of L-proline. *Planta* 154: 207-214. The resuspension medium is the same as that described above. All further Hi-II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is preferred to select the highest level of expression of polysaccharide degrading enzymes, and it is thus useful to ascertain expression levels in transformed plant cells, transgenic plants and tissue specific expression. One such method is to measure the expression of the target protein as a percentage of total soluble protein. One standard assay is the Bradford assay which is well known to those skilled in the art (Bradford, M. 1976. *Anal. Biochem.* 72:248). The biochemical activity of the recombinant protein should also be measured and compared with a wildtype standard. The activity of polysaccharide degrading enzymes can be determined by the methods described in Dai et al, supra.

A variety of assays for endo-β-1,4-glucanase, cellobiohydrolase and β-D-glucosidase are known in the art which can be used to detect enzyme activity in extracts prepared from maize callus and seeds. See, Coughlan et al. ((1988) *J. Biol. Chem.* 263:16631-16636) and Freer ((1993) *J. Biol. Chem.* 268:9337-9342). In addition, western analysis and ELISAs can be used to assess protein integrity and expression levels. Individual $T_1$ seeds are screened by the assay of choice for expression of the target protein, in this case the cellulases or β-glucosidase. The individual plants expressing the highest levels of active enzyme are chosen for field studies, which include back-crosses (See "Plant Breeding Methodology" edit. Neal Jensen, John Wile & Sons, Inc. 1988), selection for increased expression and increased seed amounts. A Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ and washed in an SDS solution. In the Western analysis, instead of isolating DNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997).

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate An initial test of enzyme function is performed with lines of processed corn seed containing single enzymes. For saccharification of cellulose, seed tissue from these lines are mixed in the appropriate ratio to produce a high specific activity for degradation of crystalline cellulose. According to Baker et al. ((1995) "Synergism between purified bacterial and fungal cellulases", in *Enzymatic Degradation of Insoluble Carbohydrates*. ACS Series 618, American Chemical Society, Washington, D.C., pp. 113-141.), maximum synergism for saccharification of cellulose is with a composite that is about 80% of the *Trichoderma reesei* CBHI (exo-β-1,4-glucanase) and about 20% of the *Acidothermus cellulolyticus* endo-β-1,4-glucanase. The addition of about 0.1% of the *Candida wickerhamii* β-D-glucosidase facilitates the degradation of short glucose oligomers (dp=2-6) to yield glucose. Later, cross pollination of the selected lines is used to produce lines that express all three of the cellulase-degrading enzymes.

The levels of expression of the gene of interest can be enhanced by the stable maintenance of a polysaccharide degrading enzyme encoding gene on a chromosome of the transgenic plant. Use of linked genes, with herbicide resistance in physical proximity to the cellulase gene, would allow for maintaining selective pressure on the transgenic plant population and for those plants where the genes of interest are not lost.

In a preferred embodiment of the invention and as also described at Methods for Cost-Effective Saccharification of Lignocelluosic Biomass, U.S. publication no. 2003-0109011, both corn seeds and corn stover are harvested by a single harvesting operation. Such a procedure allows for the cost-effective recovery of both the seeds and the stover in one pass through the field. Using this procedure the seeds are collected in a first container and the corn stover in a second container and the collection of both the seeds and the stover is carried out concurrently in a single step. Single pass harvest integrates the collection of the lignocellulosic biomass with normal crop harvest operations. With this procedure the crop residues are collected without incurring a significant additional cost to the cost of harvesting the corn crop and without causing any additional soil compaction to cultivated fields from the passage of farm machinery, with decreased time and overall costs. Such a process has been demonstrated by Quick, G. R. (Oct. 29, 2001) Corn Stover Harvesting Field Demonstration and Biomass Harvesting Colloquium, Harlan, Iowa (record and minutes of program). In this particular process an IH 1460 with a John Deere 653A row crop head was coupled to a Hesston Stakhand wagon. The machines were modified by the Iowa State Agriculture Engineering department so that two crop streams were provided. Grain was taken up into the combine bin, and whole stover with cobs collected out the back of the machine and conveyed into the Stakhand wagon. This is just one example of the type of machine that can be used in such single pass harvesting.

Following harvest, the kernels can be milled either by the wet or dry milling methods that are known in the art. When the germ is to be separated from the seed, to be practical in this process, the germ should be capable of being separated in a commercial milling process, that is a process which does not require hand separation, but can be carried out in a commercial operation. Corn seed, for example, is readily separated from the germ or embryo, where soybean embryos are of a size that the only option for separation is by hand. In instances where the only means of separation of germ is by hand, the process would not provide the cost effective advantages as provided here.

There are two major milling processes for corn. Dry milling of corn separates the germ from the endosperm. The endosperm is recovered in the form of coarse grit and corn flakes, or it may be passed through fine rollers and reduced to corn flour.

The bulk of the corn starch produced in the United States is prepared by the wet-milling process. The first step in the wet-milling process is to steep the corn kernels in an aqueous solution. Steeping the kernels serves two main purposes. First it softens the kernels for subsequent milling, and second, it allows undesired soluble proteins, peptides, minerals and other components to be extracted from the kernels. After steeping, the kernels are separated from the steep water and then wet milled. The steep water is typically concentrated by evaporation to yield a solution referred to as a corn steep liquor. Corn steep liquor typically contains about 3.5 pounds dry solids per bushel of corn kernels with a nitrogen content between 45-48% (Blanchard (1992) *Technology of Corn Wet Milling and Associated Processes*, Elsevier, N.Y.). Protein content in corn steep liquor has been estimated at about one pound per bushel of steeped corn which amounts to approximately 15-20% (w/w) of total corn kernel protein (Blanchard (1992) *Technology of Corn Wet Milling and Associated Processes*, Elsevier, N.Y.).

While typical corn wet-milling processes employ a steeping that ranges from 12 to 48 hours, other wet-milling processes such as, for example, those known as the dry-grind process and the intermittent-milling-and-dynamic-steeping process involve an initial steeping of shorter duration and can additionally involve steeping at a higher temperature. Typically, the dry-grind and intermittent-milling-and-dynamic-steeping processes involve a steeping of whole kernels for about 12 hours or less at temperatures of about 60° C. The main objective of such a short initial steeping is to hydrate the embryo or germ. Breaking open the kernel after such a short initial steeping reduces the damage to the germ as compared to dry milling. The hydrated germ can then be recovered by methods typically utilized in the wet-milling process. The degerminated kernel fraction can then be subjected to a second steeping with additional grinding or milling to facilitate removal of soluble material from the kernel particles. See, Singh and Eckhoff (1996) *Cereal Chem.* 73:716-720 and Lopes-Filho et al. (1997) *Cereal Chem.* 74:633-638.

Dry milling does not use the steeping process. The procedure can include, for example, tempering cleaned corn kernels with water or steam to bring them up to 20 to 22% moisture and the corn is then held for about one to three hours. A degerminator or impact mill is used to break open the corn. Discharge from the degerminator is dried to about 15% to 18% moisture. The germ and endosperm are separated by size and/or density, resulting in an enriched fraction for germ or endosperm. See, e.g., Watson, S., Chapter 15, "Corn Marketing, Procesing and Utilityzation" pp. 918-923, *Corn and Corn Improvement*, Eds. G. F. Sprague and J. W. Dudley, American Soc. of Agronomy, Crop Society of America, Soil Society of America, Madison, Wis. (1988).

While the invention does not depend on the use of either dry or wet milling, it is recognized that either milling method can be used to separate the germ from the endosperm. By expressing the cell wall polysaccharide-degrading enzymes of the invention under the control of an embryo-preferred promoter, these enzymes can be preferentially produced in the corn germ. Thus, the isolated germ can be used as a source of enzymes for cell wall polysaccharide degradation, and the starch-laden endosperm can be utilized for other purposes. If desired, oil can also be extracted from the germ, using solvents such as, for example, hexane, before the germ is contacted with corn stover. Methods for extracting oil from corn germ are known in the art.

With dry or wet-milling, the desired polysaccharide-degrading enzymes can be separated from the starch. As described above, a promoter that drives expression in an embryo, particularly a promoter that preferentially drives expression in the corn germ, can be operably linked to a nucleotide sequence encoding a polysaccharide-degrading enzyme of the invention. Because the germ is separated from the starch during wet milling, the germ, in the substantial absence of kernel starch, can be used as the enzyme source for degradation of cell wall polysaccharides in the corn stover. While the corn starch can be used for any purpose or in any process known in the art, the starch can also be used for the production of ethanol by methods known in the art. If desired, the starch can be used for ethanol production together with the corn stover. Thus, the starch can be recombined with the germ or combined with the stover or the stover-germ mixture. Starch-degrading enzymes are then utilized to degrade the starch into glucose for fermentation into ethanol.

Although the methods of the invention can be used for the saccharification of plant cell wall polysaccharides in any of the processes in which saccharification is desired, such as animal feed additives, gene treatment, and preferably, in the subsequent fermentation into ethanol, the invention does not depend on the production of ethanol. The invention encompasses any fermentative method known in the art that can utilize the fermentable sugars that are produced as disclosed herein. Such fermentative methods also include, but are not limited to those methods that can be used to produce lactic acid, malonic acid and succinic acid. Such organic acids can be used as precursors for the synthesis of a variety of chemical products that can be used as replacements for similar products that are currently produced by petroleum-based methods. See, United States Department of Energy Fact Sheets DOE99-IOFC17 (1999), DOE99-IOFC21 (1999), and DOE/GO-102001-1458 (2001).

With transgenic plants according to the present invention, polysaccharide degrading enzymes can be produced in commercial quantities. Thus, the selection and propagation techniques described above yield a plurality of transgenic plants that are harvested in a conventional manner. The plant seed expressing the recombinant polysaccharide degrading enzymes can be used in a commercial process, or the polysaccharide degrading enzymes extracted. When using the seed itself, it can, for example, be made into flour and then applied in the commercial process. Polysaccharide degrading enzyme extraction from biomass can be accomplished by known methods. Downstream processing for any production system refers to all unit operations after product synthesis, in this case protein production in transgenic seed (Kusnadi, A. R., Nikolov, Z. L., Howard, J. A., 1997. *Biotechnology and Bioengineering*. 56:473-484). Seed is processed either as whole seed ground into flour, or fractionated and the germ separated from the hulls and endosperm. If germ is used, it is usually defatted using a hexane extraction and the remaining crushed germ ground into a meal or flour. In some cases the germ is used directly in the industrial process or the protein can be extracted (See, e.g. WO 98/39461). Extraction is generally made into aqueous buffers at specific pH to enhance recombinant protein extraction and minimize native seed protein extraction. Subsequent protein concentration or purification can follow. In the case of industrial enzymes, concentration through membrane filtration is usually sufficient.

Following the degradation or saccharification of cell wall polysaccharides, the fermentable sugars that result therefrom can be converted into ethanol via fermentation methods employing microorganisms, particularly yeasts and/or bacteria. Such microorganisms and methods of their use in ethanol production are known in the art. See, Sheehan 2001. "The road to Bioethanol: A strategic Perspective of the US Department of Energy's National Ethanol Program" In: Glucosyl Hydrolases For Biomass Conversion. ACS Symposium Series 769. American Chemical Society, Washington, D.C. Existing ethanol production methods that utilize corn grain as the biomass typically involve the use of yeast, particularly strains of *Saccharomyces cerevisiae*. Such strains can be utilized in the methods of the invention. While such strains may be preferred for the production of ethanol from glucose that is derived from the degradation of cellulose and/or starch, the methods of the present invention do not depend on the use of a particular microorganism, or of a strain thereof, or of any particular combination of said microorganisms and said strains.

Furthermore, it is recognized that the strains of *Saccharomyces cerevisiae* that are typically utilized in fermentative ethanol production from corn starch might not be able to utilize galacturonic acid and pentose sugars such as, for example, xylose and arabinose. However, strains of microorganisms are known in the art that are capable of fermenting these molecules into ethanol. For example, recombinant *Saccharomyces* strains have been produced that are capable of simultaneously fermenting glucose and xylose to ethanol. See, U.S. Pat. No. 5,789,210, herein incorporated by reference. Similarly, a recombinant *Zymomonas mobilis* strain has been produced that is capable of simultaneously fermenting glucose, xylose and arabinose to produce ethanol. See, U.S. Pat. No. 5,843,760; herein incorporated by reference. See, also U.S. Pat. Nos. 4,731,329, 4,812,410, 4,816,399, and 4,876,196, all of which are herein incorporated by reference. These patents disclose the use of *Z. mobilis* for the production of industrial ethanol from glucose-based feedstocks. Finally, a recombinant *Escherichia coli* strain has been disclosed that is able to convert pure galacturonic acid to ethanol with minimal acetate production. See, Doran et al. ((2000) *Appl. Biochem. Biotechnol.* 84-86:141-152); herein incorporated by reference.

The methods of the invention involve obtaining plant tissue that expresses at least one of the cell wall-polysaccharide-degrading enzymes of the invention and lignocellulosic biomass. Any plant tissue where the enzyme expresses can be used in the invention, including, for example, leaf, stem, root, tassel, anther, pollen, seed, ovules, or any other tissue of the plant. In an embodiment the plant tissue may be leaf. In another embodiment, the plant tissue is a seed or part thereof. The plant tissue may be in another embodiment a grain seed or part thereof. In yet another embodiment, the plant tissue is a corn kernel or part thereof, such as, for example, an embryo that is also referred to as the germ. More than one plant tissue may be the source of one or more enzymes. The lignocellulosic biomass can originate from the same plants as the plant tissue or from different plants. Preferably, the lignocellulosic biomass comprises plant residues. More preferably, the lignocellulosic biomass comprises crop residues left in the field after the harvest of corn grain, which is also known as corn stover. Most preferably, the lignocellulosic biomass comprises corn stover that is from the same plants as the cell wall polysaccharide-degrading enzymes for increased cost efficiency.

The lignocellulosic biomass is contacted with the plant tissue and exposed to conditions favorable for the degradation of the polysaccharides in the lignocellulosic biomass. Prior to contacting the lignocellulosic biomass with the plant tissue, the plant tissue, the lignocellulosic biomass, or both, can be pretreated or processed in any manner known in the art that would enhance the degradation of the polysaccharides. For example, the lignocellulosic biomass can be processed by being chopped, sliced, minced, ground, pulverized, crushed, mashed or soaked. The plant tissue, such as the seed, containing the enzymes can be treated with dry or wet-milling processes. Such processing can also include incubating the plant tissue and/or lignocellulosic biomass in a solution, particularly an aqueous solution. If desired, the solution can be agitated, mixed, or stirred. The solution can comprise any components known in the art that would favor extraction of an active enzyme from the plant tissue and/or enhance the degradation of cell wall polysaccharides in the lignocellulosic biomass. Such components include, but are not limited to, salts, acids, bases, chelators, detergents, antioxidants, polyvinylpyrrolidone (PVP), polyvinylpolypyrrolidone (PVPP), and $SO_2$. Furthermore, specific environmental conditions, such as, for example, temperature, pressure, pH, $O_2$ concentration, $CO_2$ concentration, and ionic strength, can be controlled during any processing and/or subsequent steps to enhance polysaccharide degradation and/or ethanol production.

In certain embodiments of the invention, it may be desired to process the plant tissue so as to produce an extract comprising the polysaccharide-degrading enzyme and then contacting the lignocellulosic biomass with the extract. The processing of the plant tissue to prepare such an extract can be accomplished as described supra, or by any method known in the art for the extraction of an enzyme from plant tissue. In other embodiments of the invention, the plant tissue and the lignocellulosic biomass may be combined and then processed as described supra. See, e.g., Henry & Orit (1989) *anal. Biochem.* 114:92-96.

In yet another embodiment of the invention, prior to contacting the lignocellulosic biomass with the plant tissue or extract thereof, the lignocellulosic biomass can be prepared by pretreating the lignocellulosic biomass by methods known in the art (Nguyen et al. 1996. NREL/DOE Ethanol Pilot Plant: Current Status and Capabilities. Bioresource Technology 58:189-196). In the pretreatment step, the hemicellulosic fraction of the feedstock is hydrolyzed to soluble sugars. This step also increases the enzymes's ability to convert the major fraction of the feedstock (cellulose) to soluble glucose. The pretreatment step mixes the feedstock with sulfuric acid and water (approximately 1% acid in the final solution), then raises the slurry (20-25% solids) to reaction temperature (160-200° C.) with steam. The mixture is held at the reaction temperature for a predetermined time (2-20 min) then flashed into a tank maintained at near atmospheric pressure. Because of the sudden pressure drop, a fraction of the steam condensate and volatile compounds formed during the heating is evaporated and removed as flash tank overhead, which is condensed and sent to waste treatment. Lime is added to the remaining slurry to adjust the pH to 4.5.

While the cell wall polysaccharides are degraded prior to utilization of the fermentable sugars by microorganisms, the methods are not limited to a saccharification step which precedes the fermentation step. In certain embodiments of the invention, a single combined saccharification/fermentation step can be employed in the methods of the invention. In other embodiments, saccharification is initiated before fermentation and can be fully or partially complete prior to the initiation of the fermentation.

The methods of the invention find use with any plant species capable of producing a polysaccharide-degrading enzyme of the invention. Preferably, the plant species are crop plant species. More preferably, the plant species are selected from the grain and oilseed plants. Most preferably, the plant species is corn.

The following illustrates, but is not intended to limit the scope of the invention. It will be evident to one skilled in the art that variations and modifications are possible and fall within the scope and spirit of the invention.

EXAMPLE 1

Preparation of Plasmids

FIG. 1 shows the E1 vector, having the E1 cellulase sequence (FIG. 2, SEQ ID NO: 1), the seed-preferred promoter PGNpr2 (supra), the KDEL (SEQ ID NO: 12) endoplasmic reticulum retention sequence shown in FIG. 4A (SEQ ID NO: 2); the barley alpha-amylase signal sequence, (BAASS), which was optimized and is shown in FIG. 4B (SEQ ID NO: 3), and a pin II terminator, supra. The 35S promoter, supra, drives the selectable marker, the maize optimized PAT gene. The gene confers resistance to bialaphos. See, Gordon-Kamm et al, *The Plant Cell* 2:603 (1990); Uchimiya et al, *Bio/Technology* 11:835 (1993), and Anzai et al, *Mol. Gen. Gen.* 219:492 (1989). The E1 cellulase gene from *Acidothermus cellulolyticus* was received from NREL. For expression in maize, the first 40 amino acids were optimized to maize preferred codons. The BAASS and KDEL (SEQ ID NO: 12) sequences were added to the gene by PCR using the NREL clone as template. The PCR product moved to a PCR-ready cloning vector, then moved to an intermediate vector to add the pin II terminator sequence, and then shuttled into the plant expression vector as a complete unit. PGNpr2 is just upstream of the E1 gene.

Figure 3:
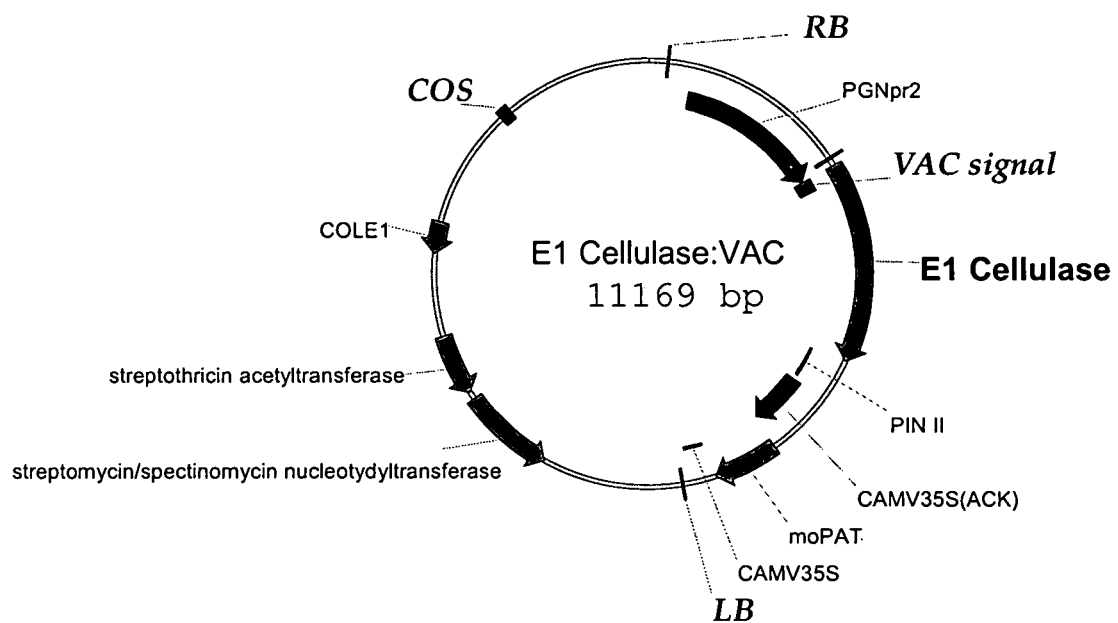
FIG. 3 is a construct map showing the construct for expressing E1 cellulase targeted to the vacuole.

FIG. 3 shows the E1 construct where the vacuole signal sequence is substituted for the BAASS sequence. The vacuole targeted version of the E1 cellulase gene was constructed by adding the vacuole leader to the codon preferred optimized E1 gene generated in a previous construct (BAASS:E1) using PCR. This PCR product was cloned into the intermediate vector to add the pin II terminator and then transferred to the plant expression vector behind promoter PGNpr2. The vacuole signal sequence is shown in FIG. 4A (SEQ ID NO:2).

Figure 5:
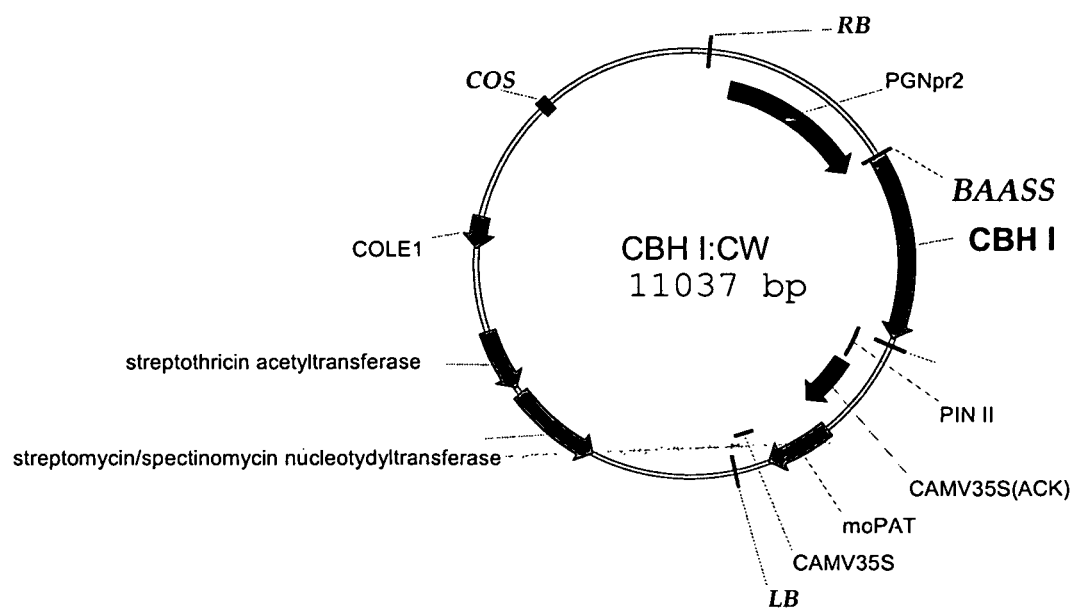
FIG. 5 is a construct map showing the construct for expressing CBH I such that it is secreted to the cell wall.

FIG. 5 shows the CBH I gene construct, similar to the E1 construct but in this case having the BAASS sequence only, such that the enzyme is secreted to the cell wall. The starting CBH I clone was received from NREL. This gene most closely matches the CBH I gene from *Trichoderma koningii* at the nucleic acid level. The gene was maize optimized for the first 40 amino acids using a PCR based mutagenesis approach—this includes the 24 amino acid BAASS sequence. Codons D346 and D386 were also maize codon optimized to remove the potentially destabilizing sequences at those positions. The CBH I sequence used is shown in FIG. 6 (SEQ ID NO: 4). The BAASS sequence was added to the optimized CBH I gene by PCR. The PCR product was moved to an PCR-ready cloning vector to add the pin II terminator, and then the whole unit was transferred to the transformation vector. The promoter PGNpr2 is used to drive the transcription of CBH I coding sequence.

Figure 7:
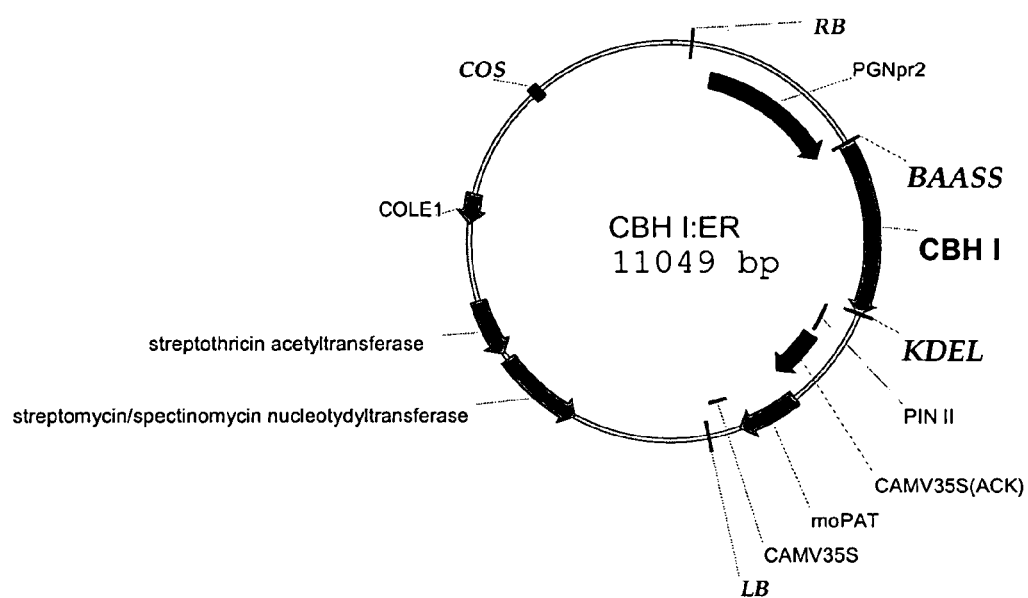
FIG. 7 is a construct map showing the construct for expressing CBH I retained in the endoplasmic reticulum (KDEL is disclosed as SEQ ID NO: 12).
Figure 8:
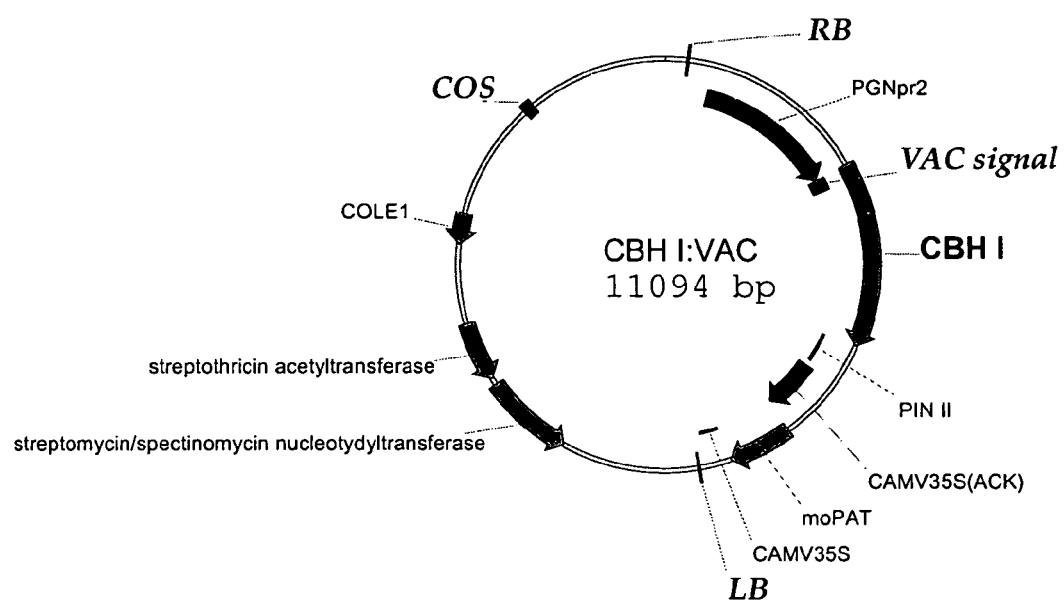
FIG. 8 is a construct map showing the construct for expressing CBH I targeted to the vacuole.

FIG. 7 shows the CBH I vector, which is similar to the E1 vector targeted to the endoplasmic reticulum. FIG. 8 shows the CBH I vector, which is similar to the E1 vector targeted to the vacuole.

EXAMPLE 2

Transformation of Maize

Fresh immature zygotic embryos were harvested from Hi-II maize kernels at 1-2 mm in length. The general methods of Agrobacterium transformation were used as described by Japan Tobacco, at Ishida et al. 1996. "High efficiency transformation of maize (*Zea mays* L.) mediated by *Agrobacterium tumefaciens*" Nature Biotechnology 14:745-750 with the modifications described supra. Fresh embryos were treated with 0.5 ml log phase *Agrobacterium* strains EHA101. Bacteria were grown overnight in a rich medium with kanamycin and spectinomycin to an optical density of 0.5 at 600 nm, pelleted, then re-inoculated in a fresh 10 ml culture. The bacteria were allowed to grow into log phase and were harvested at no more dense than OD600=0.5. The bacterial culture is resuspended in a co-culture medium.

For stable transformations, embryos were transferred to a bialaphos selective agent on embryogenic callus medium and transferred thereafter every two weeks to allow growth of transformed type II callus. Plants were regenerated from the callus.

EXAMPLE 3

Enzyme Analysis

Six single seed from each plant (up to 10 plants per event) were assayed separately. Each seed was pulverized in an automatic seed pounder and extracted in a high-speed shaker in 1 ml of 50 mM sodium acetate, pH 5. Cell debris was pelleted and the supernatant recovered for analysis of 1) total soluble protein using the Bradford assay (Bradford, M. 1976. *Anal. Biochem.* 72:248) and 2) the concentration of the target protein using the assay described below.

The E1 enzyme concentration was determined through the following activity assay. The assay is performed in a microtiter plate format. An appropriate amount of extract from transgenic seed containing 1 ug of TSP is transferred to a well of a 96-well microtiter plate. The total sample volume is brought to 0.1 ml with the addition of extraction/reaction buffer. The reaction is started with the addition of 0.025 mL of 5 mM 4-methylumbelliferyl-m-D-cellobioside (MUC). The reaction is incubated at 50° C. for 30-45 minutes. At each reading time, 0.025 mL of the reaction mix is pipetted into 0.175 mL of stop buffer (0.2 M $Na_2CO_3$), then the amount of fluorescence is read at 460 nm with excitation of 360 nm, and enzyme concentration determined in relation to a standard curve generated with purified enzyme spiked into corn seed extract.

The CBH I enzyme concentration is determined through exactly the same procedure except that the incubation time is extended to two hours before reading the fluorescence on the plate.

EXAMPLE 4

Increasing Expression Levels and Agronomic Yield Through Breeding

The Hi-II maize line that is used in tissue culture for plant transformation shows poor agronomic characteristics and is not high-yielding in the field. However, one of the most important goals for industrial protein production is yield near that of commercial corn lines. Thus, agronomic quality of early transgenic material can be improved through breeding the transgenic plant into plants with improved agronomic characteristics and/or which have characteristics that provide for improved expression of the enzyme. To accomplish this, $T_1$ seed from selected high-cellulase-expressing independent lines was planted in nurseries and crossed to elite inbreds. The goal is to develop high-yielding hybrids with good agronomic qualities. Improved expression levels are expected by breeding into elite varieties using the backcrossing methods described, supra.

Crossing the Hi-II events with Stiff Stalk elite germplasm in particular can also increase event recovery. (See U.S. Ser. No. 10/349,392, to be published; Horn, Michael E.; Harkey, Robin L.; Vinas, Amanda K.; Drees, Carol F.; Barker, Donna K.; and Lane, Jeffrey R., "Use of HiII-Elite Hybrids in *Agrobacterium*-based Transformation of Maize" *In Vitro Cell. Dev. Biol.-Plant.* (In press)). Stiff Stalk inbreds have been available since at least about the 1950s and are derived from the Iowa Stiff Stalk synthetic population. Sprague, G. F. "Early testing of inbred lines of maize" *J. Amer. Soc. Agron.* (1946)38:108-117; for examples see PI accession no. 550481 and discussion of Stiff Stalk germplasm at U.S. Pat. Nos. 5,706,603; 6,252,148; 5,245,975; 6,344,599; 5,134,074; and Neuhausen, S. "A survey of Iowa Stiff Stalk parents derived inbreds and BSS(HT)C5 using RFLP analysis" *MNL* (1989) 63:1.10-111.

In this instance, the transgenic plant was crossed into elite Stiff Stalk elite plants, SP122. Improved expression of cellulases often times levels achieved in Hi-II is expected. In each generation, the highest expressing ears showing agronomic promise are selected and seed replanted from those ears in subsequent nurseries. After pollination, maturation and harvest, 50 seed from each progeny ear are combined, ground and analyzed for expression levels of extractable cellulase. Only those showing improvement in the amount of cellulases are selected for replanting. At each generation, approximately the top 10% of lines are replanted for the breeding program.

EXAMPLE 5

Expression of Cellulases in Plants

Figure 9:
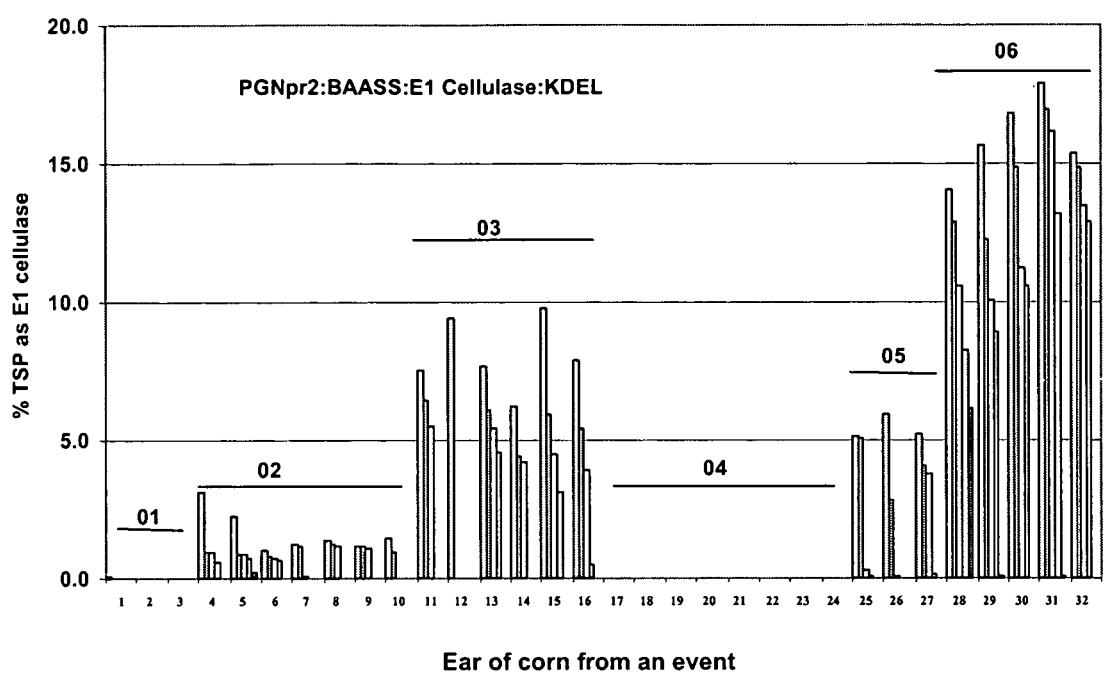
FIG. 9 is a graph depicting the results of expression of E1 cellulase, in percent of total soluble protein, retained in the endoplasmic reticulum (KDEL is disclosed as SEQ ID NO: 12).
Figure 10:
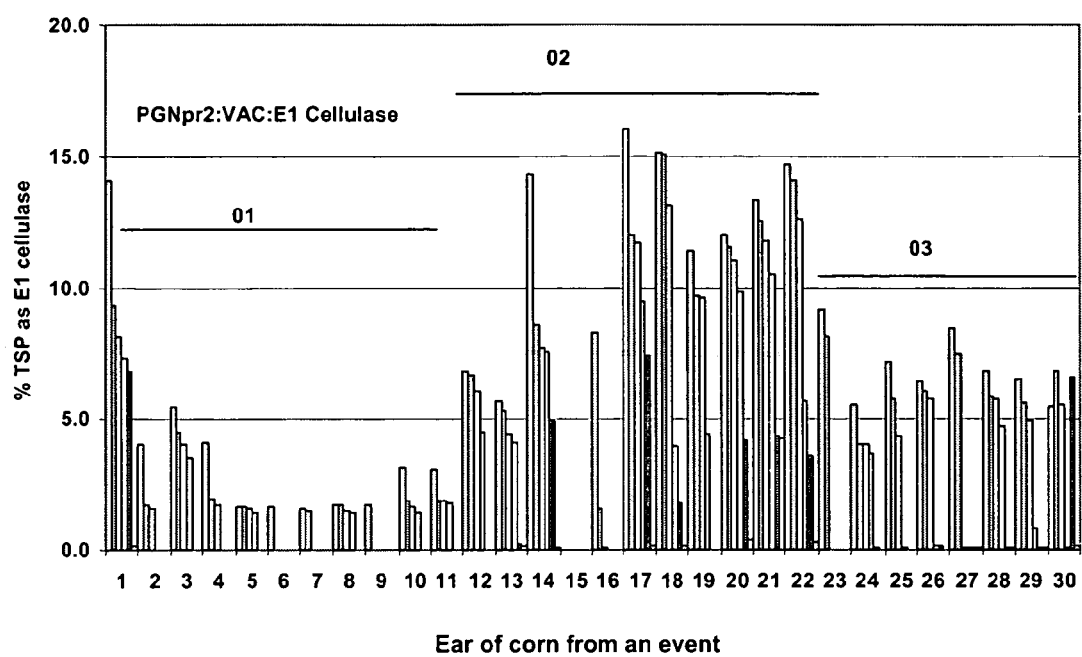
FIG. 10 is a graph depicting the results of expression of E1 cellulase, in percent of total soluble protein, when targeted to the vacuole.

The results of expression of the E1 cellulase, when targeted to the ER are shown in FIG. 9. The numbers on the x-axis represent an ear of corn from an event. The ears are grouped by the event which produced the ear, as shown by the number above each group. For each ear of corn, six individual seeds were assayed for total soluble protein. Expression levels were impressive with values greater than 15% TSP, however a few events did not express detectable amounts of E1 cellulase. Even better expression was obtained when the E1 cellulase was retained in the vacuole, as shown in FIG. 10. While fewer events were recovered, all lines showed expression of E1 cellulase, with the best line in each event ranging from 8% TSP to more than 15% TSP.

Figure 11:
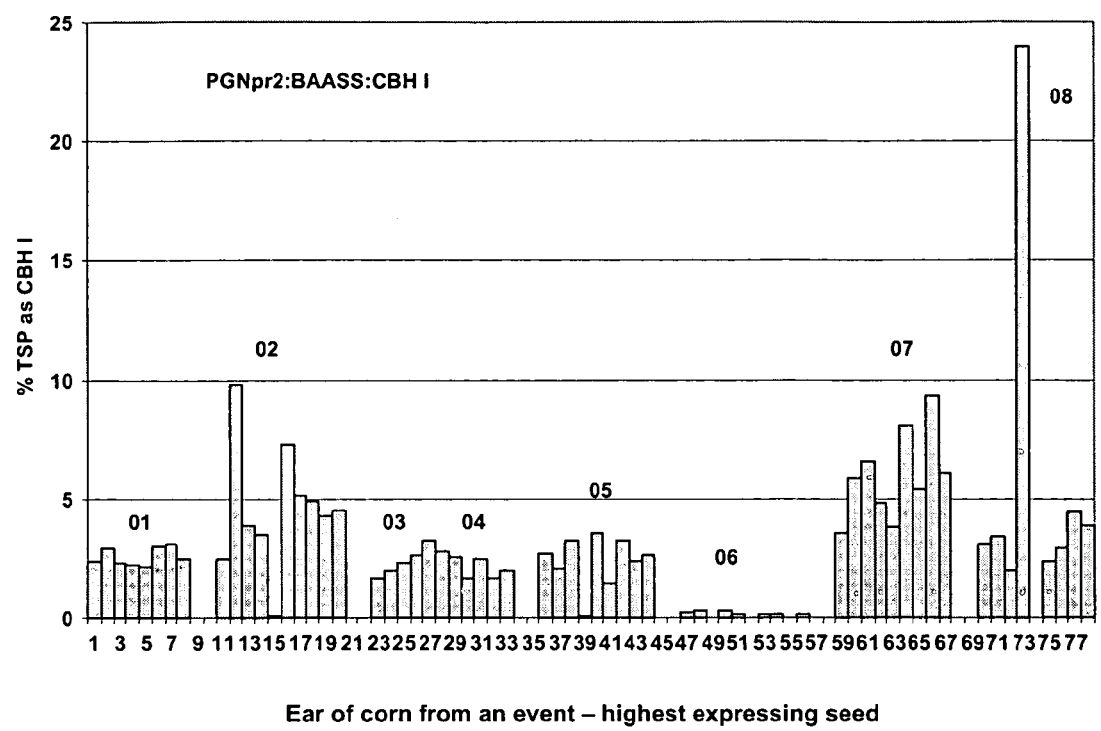
FIG. 11 is a graph depicting the results of expression of CBH I, in percent of total soluble protein, when secreted to the cell wall.

Expression of the CBH I enzyme, where secreted to the cell wall is graphed in FIG. 11. In this graph and in FIG. 12, the numbers on the x-axis represent a selected ear of corn produced from an event. The ears are grouped by the event which produced the ear, as shown by the number above each group In this instance, the highest expressing seed was assayed for total soluble protein. Overall, high expression levels were obtained, with the top line containing 23% TSP as CBH I.

Figure 12:
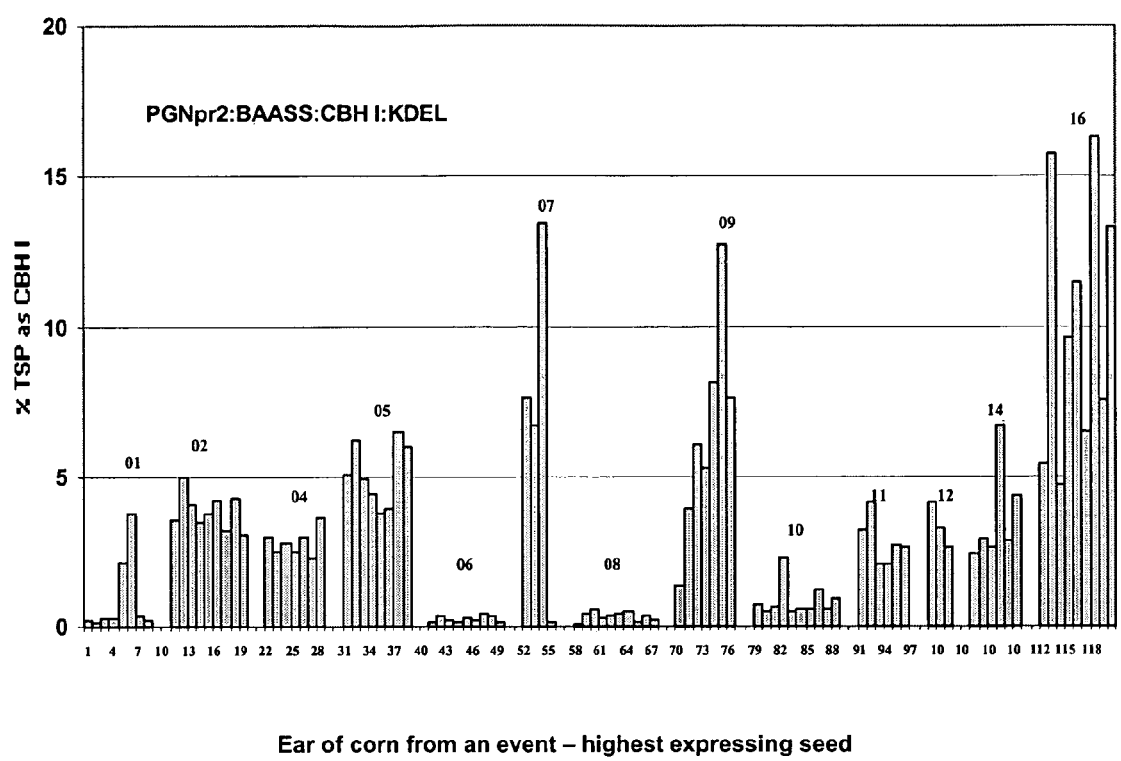
FIG. 12 is a graph depicting the results of expression of CBH I, in percent of total soluble protein, when retained in the endoplasmic reticulum (KDEL is disclosed as SEQ ID NO: 12).

Even better results were obtained by targeting CBH I to the ER. FIG. 12 shows that a greater fraction of events contained lines expressing CBH I at levels greater than both 5% and 10% TSP. These high expression results are extremely significant because the CBH I enzyme has not been recovered previously at high expression levels in any plant or fungal system. The highest expression published to date is 0.02% TSP in tobacco leaves (Ziegelhoffer et al, supra). Thus, the highest single seed levels at 23% TSP are 1000 fold higher than the next best system. However, use of a vacuole retention sequence resulted in plants with no enzyme expressed.

Levels of enzymatically active cellulases that are produced in transgenic plants are commercially very attractive. Levels of 10% TSP are considerably higher than those obtained by conventional means and are higher than other attempts at expression, other than the commercially unfeasible *Arabidposis*. Table 4 summarizes the potential of using corn to produce cellulases. High expression combined with the significant production scalability and storage of enzyme in grain demonstrates the advantages of the maize system.

TABLE 4

Heterologous cellulase expression in corn and production potential.

| Enzyme | Gene source | Transgenic plant system | Expression level | Stable storage | Scalability[1] |
| --- | --- | --- | --- | --- | --- |
| Endo-1,4-β-D-glucanase | Bacterial (*Acidothermus*) | Corn (vacuole targeted) | 16% TSP in seed | Yes | +++ |
| Endo-1,4-β-D-glucanase | Bacterial (*Acidothermus*) | Corn (ER targeted) | 18% TSP in seed | Yes | +++ |
| Cellobiohydrolase | Fungal (*Trichoderma reesei*) | Corn (cell wall targeted) | 23% TSP in seed | Yes | +++ |
| Cellobiohydrolase | Fungal (*Trichoderma reesei*) | Corn (ER targeted) | 16% TSP in seed | Yes | +++ |

[1]Scalability defined by 2002 US crop acreage, scale-up potential: −, unscalable; +, fair; ++, moderate; +++, significant.

EXAMPLE 6

Transformation With Exocellulase and Endocellulase Sequences

In further exemplification of the invention, additional exocellulase and endocellulase encoding sequences were transformed into plants.

Figure 13:
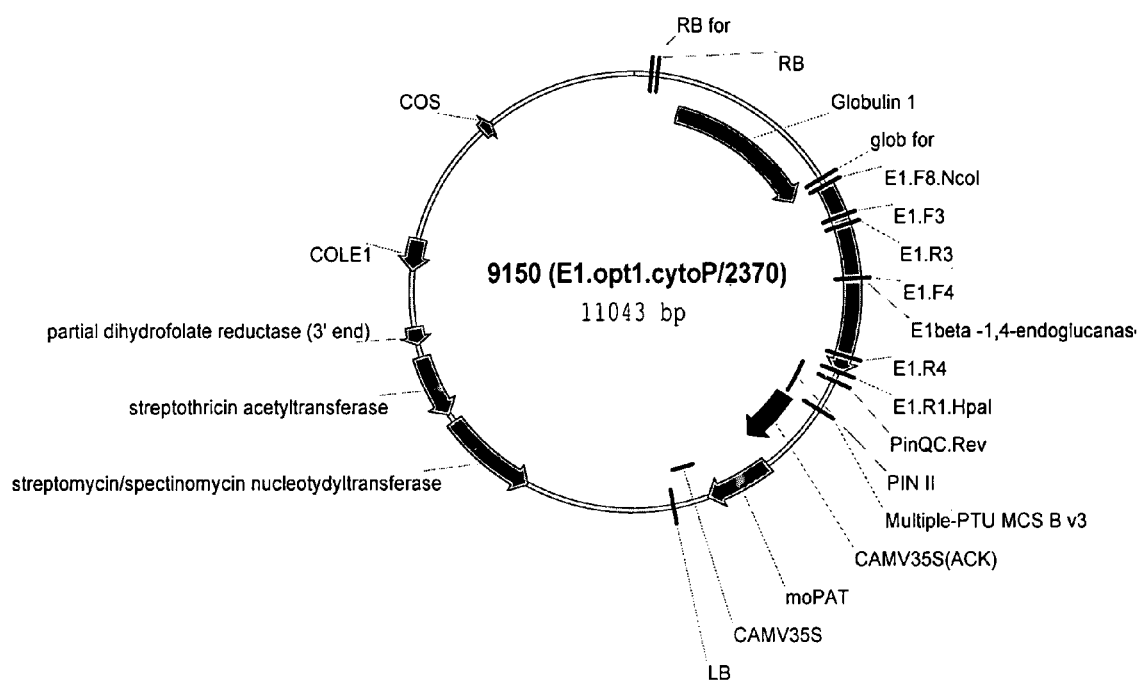
FIG. 13 is a construct map showing the construct for cytoplasmic expression of E1.
Figure 14:
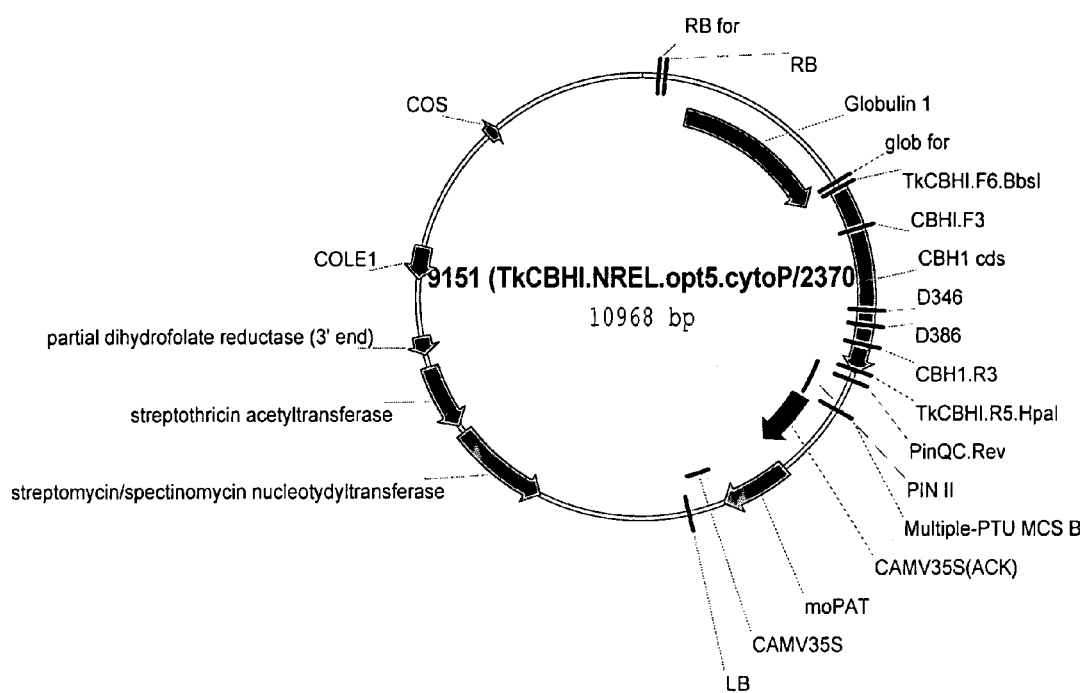
FIG. 14 is the construct map showing the construct for cytoplasmic expression of CBH I

Two vectors were prepared expressing the E1 and CBH I cellulases described supra in the cytoplasm. The vector for expression of E1 is shown in FIG. 13, driven by the globulin-1 promoter PGNpr2, supra. The vector for cytoplasmic expression of CBH I is shown in FIG. 14.

Figure 17:
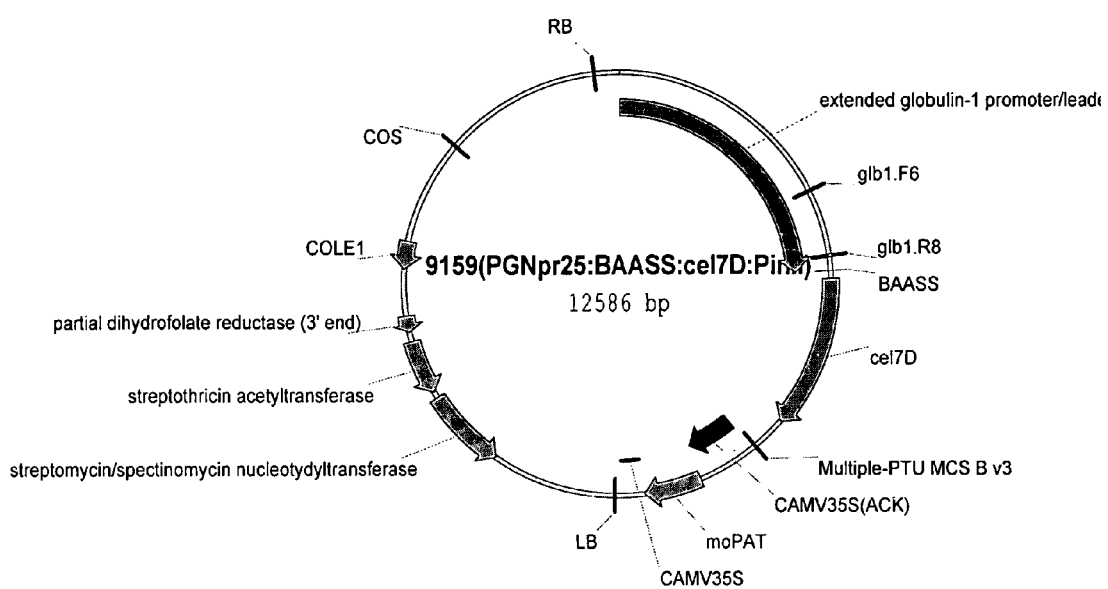
FIG. 17 is the construct map showing the construct for expression of cbh1-4 secreted to the cell wall.

A BAASS signal sequence (in italics in FIG. 15, SEQ ID NO: 5) was used with the exocellulase gene cel7D (also known as cbh1-4 from *Phaneorchaete chrysosporium* (the genomic is shown in Gen Bank accession L22656) lacking the native signal sequence, the sequence used in this instance was received from Dan Cullen of Forest Products and is set forth in FIG. 15 (SEQ ID NO: 6). In this instance an extended globulin-1 promoter as represented in FIG. 16 (SEQ ID NO: 7) was used to drive expression in the cell wall targeted construct. The final vector for plant transformation, pAB 19159 is shown in FIG. 17.

Figure 19:
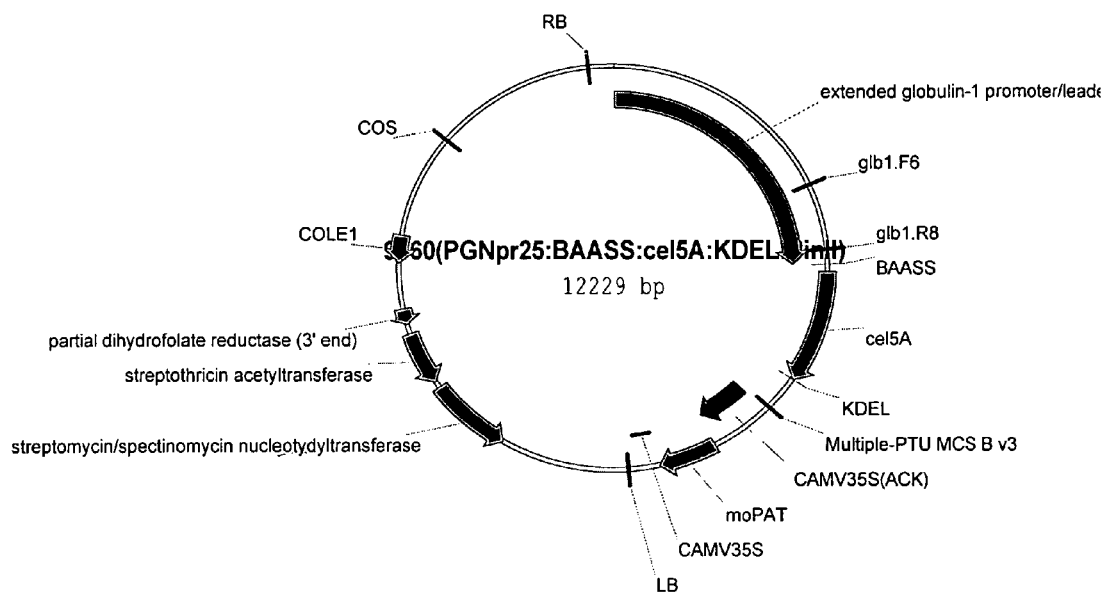
FIG. 19 is the construct map showing the construct for expression of cel5A retained in the endoplasmic reticulum (KDEL is disclosed as SEQ ID NO: 12).

The endocellulase gene cel5A from *Phaneorchaete chrysosporium* (the genomic is shown in GenBank accession AY682743) lacking the native signal sequence, was also received from Forest Products and is SEQ ID NO: 8, shown in FIG. 18. It was used with a BAASS sequence of SEQ ID NO: 5 (here in italics) and with a KDEL (SEQ ID NO: 12) sequence, in bold (SEQ ID NO: 9). The final vector for plant transformation, pAB19160, shown in FIG. 19, contains the extended globulin-1 promoter of SEQ ID NO: 7, in this vector driving expression of an endoplasmic reticulim targeted version of the cel5A gene product.

Figure 21:
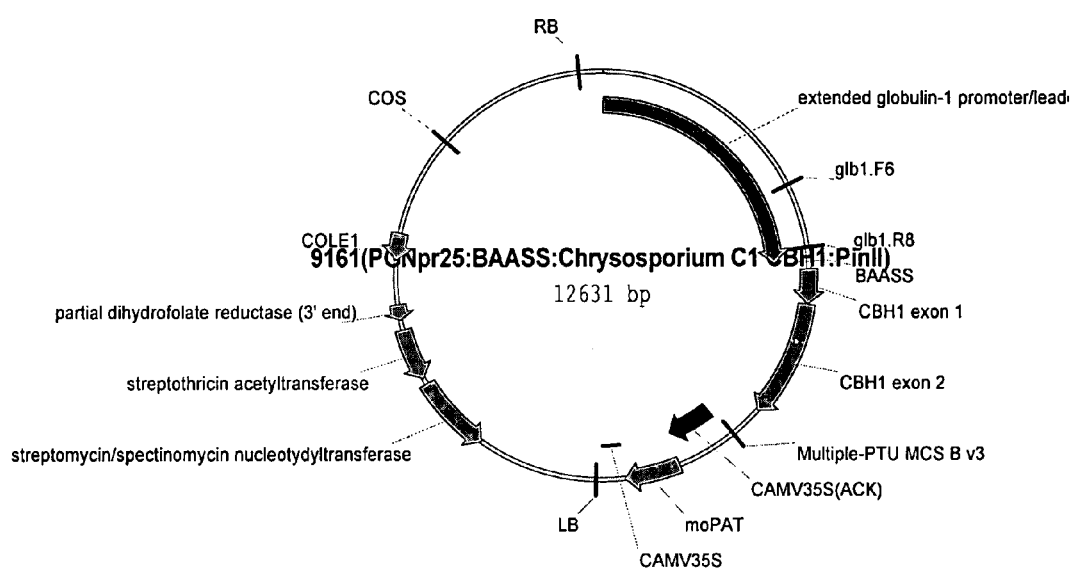
FIG. 21 is the construct map showing the construct for expression of the *P. chrysosporium* C1 CBH I secreted to the cell wall.

The exocellulase gene from *Phanerochaete chrysosporium* C1 encoding CBH I was received from Dyadic (See U.S. Pat. No. 6,573,086) and the sequence shown in FIG. 20 (SEQ ID NO: 10) along with the BAASS sequence of SEQ ID NO: 5. The final vector for plant transformation, shown in FIG. 21, contains the extended globulin-1 promoter, supra, driving expression of a cell wall targeted version of CBH I lacking the native signal sequence.

Figure 23:
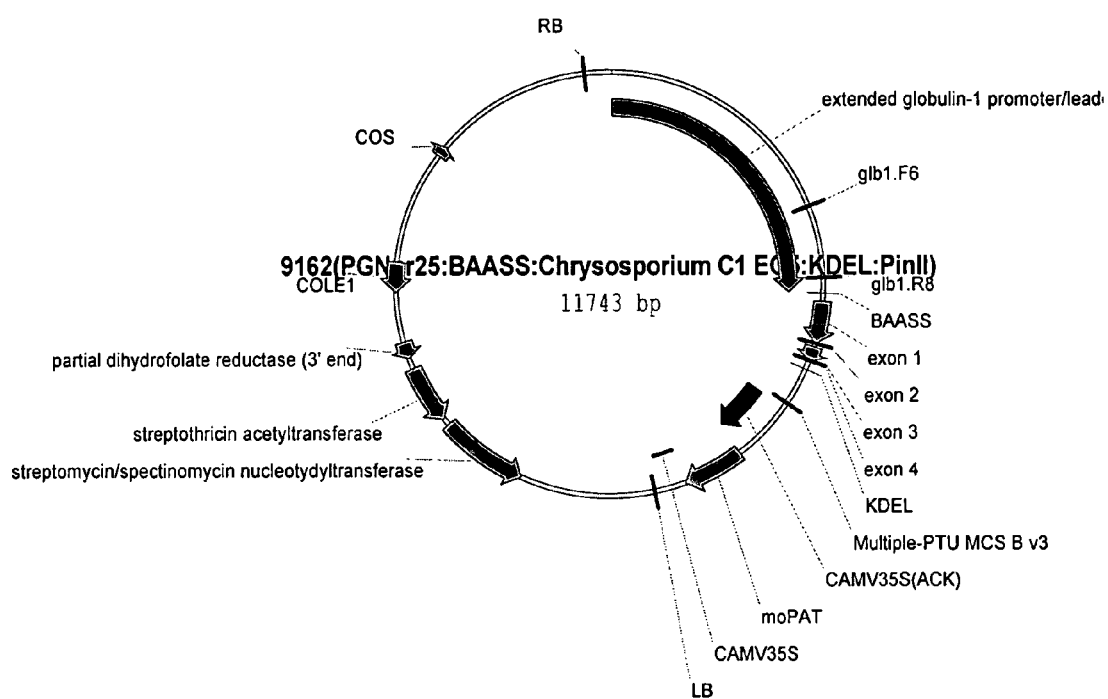
FIG. 23 is the construct map showing the construct for expressing EG5 retained in the endoplasmic reticulum (KDEL is disclosed as SEQ ID NO: 12).

The endocellulase gene from *Phanerochaete chrysosporium* C1 encoding EG5, shown in FIG. 22, was received from Dyadic (See '086 patent; SEQ ID NO: 11) along with the BAASS sequence (in italics) of SEQ ID NO: 5 and the KDEL (SEQ ID NO: 12) sequence (in bold) of SEQ ID NO: 9. The final vector for plant transformation, shown in FIG. 23, contains the extended globulin-1 promoter, supra, driving expression of an endoplasmic reticulum targeted version of EG5 lacking the native signal sequence.

EXAMPLE 7

Use of the Enzyme in Ethanol Production

Figure 24:
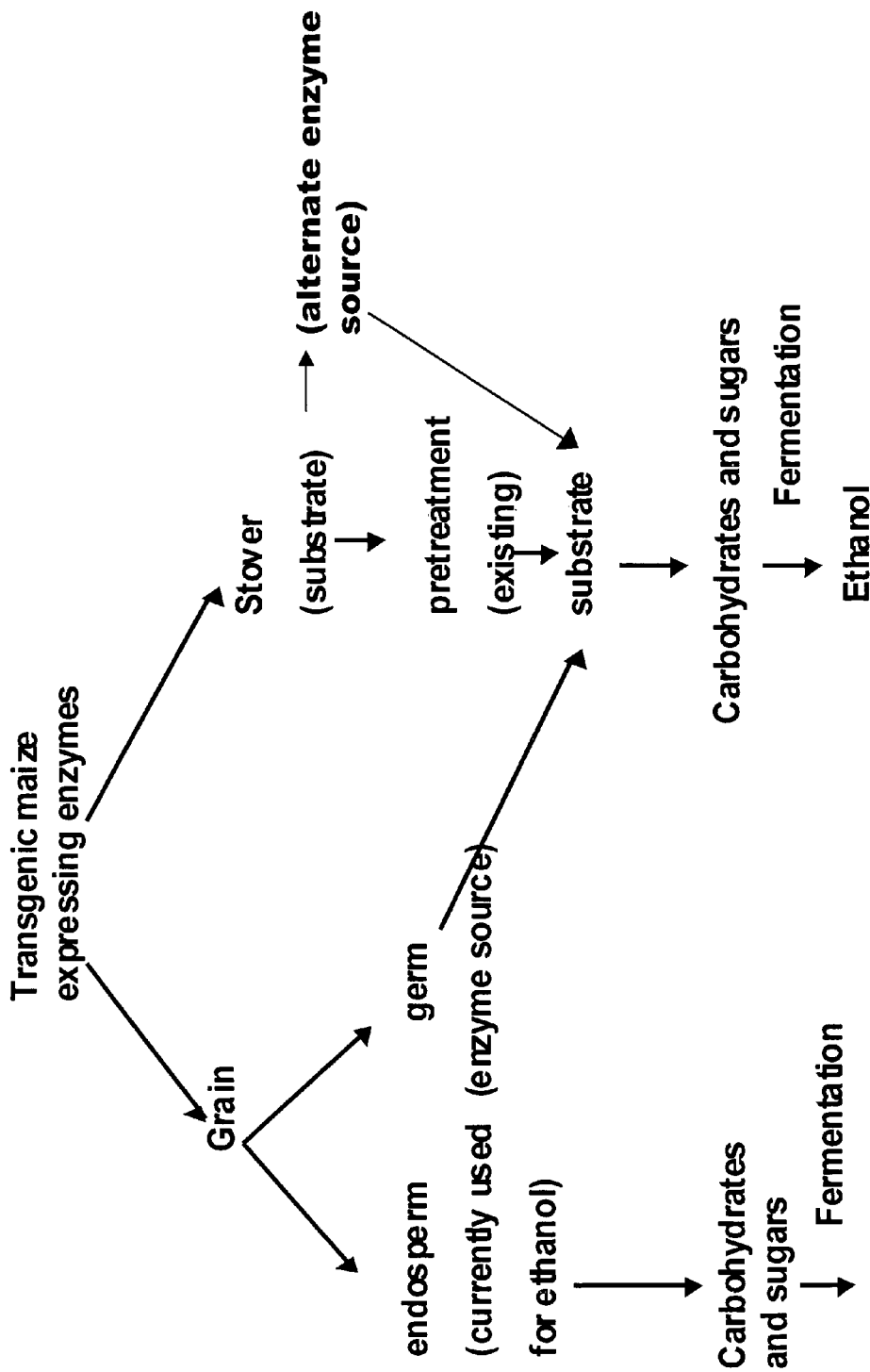
FIG. 24 is a schematic diagram which shows an embodiment of the invention which comprises an integrated process for the production of ethanol from corn stover.

In an embodiment of the invention, maize plants are genetically engineered to produce large amounts (beginning at 0.1% of whole seed or embryo dry weight) of active bacterial or fungal polysaccharide degrading enzymes in grain. Corn grain that expresses the desired cellulases is grown and harvested. The corn grain can be economically transported (low water content) and fractionated using either a wet or dry milling process to produce a enzyme-rich fraction that can be employed in conversion of a variety of lignocellulosic feedstocks. The paradigm illustrated in FIG. 24 is even more cost—effective if a single pass harvesting of stover—the lignocellullosic biomass feedstock—and grain—the enzyme source—an be implemented.

Therefore, this invention allows the production of polysaccharide degrading enzymes in amounts that far exceed the current capacity of traditional recombinant protein sources such as filamentous fungi or bacteria. Thus it is evident that the invention accomplishes at least all of its objectives.

What is claimed is:

1. A method of increasing expression in a plant seed of a first nucleic acid molecule encoding a cellulase enzyme, the cellulase enzyme comprising an exo-1,4-β-glucanase enzyme, the method comprising incorporating said first nucleic acid molecule into a nuclear chromosome of a plant cell, said first nucleic acid molecule further comprising a promoter that functions in seeds operably linked to the molecule encoding the enzyme, and said first nucleic acid molecule further comprising a nucleotide sequence encoding a signal peptide effective for directing said enzyme into the secretory pathway, and said first nucleic acid molecule optionally further comprising a nucleotide sequence encoding an endoplasmic reticulum (ER) retention signal; wherein said enzyme is targeted to the cell wall or retained in the endoplasmic reticulum, and wherein expression of said enzyme is at higher levels than levels of expression for said enzyme when targeted to the vacuoles of said plant, such that said enzyme is expressed at levels of at least 1% total soluble protein in said seed.

2. A method of reducing costs of polysaccharide degradation of polysaccharides in plant biomass, comprising:
   (a) transforming a plant cell with a first nucleic acid molecule expressing an exo-1,4-β-glucanase enzyme such that said first nucleic acid molecule is incorporated into a nuclear chromosome of said plant cell, said first nucleic acid molecule operably linked to a second nucleic acid molecule directing expression of said enzyme at higher levels in seed cells of said plant than in other cells of said plant, and a third nucleic acid molecule encoding an amino acid sequence directing said enzyme into the secretory pathway, and, optionally, a fourth nucleic acid molecule comprising a nucleotide sequence encoding an endoplasmic reticulum (ER) retention signal; wherein said enzyme is targeted to the cell wall or retained in the ER of said seed cell;
   (b) producing a plant expressing the enzyme from the plant cell and expressing said enzyme at levels of at least about 1% total soluble protein of seed of said plant;
   (c) producing a biomass of plants comprising the plant or progeny of the plant comprising the first, second, third, and fourth nucleic acid molecules such that at least one of the plants of the biomass expresses the enzyme;
   (d) harvesting the biomass; and
   (e) contacting at least a portion of the biomass with the enzyme expressed in the plant or the progeny under conditions such that the enzyme degrades the polysaccharides of at least a portion of the biomass.

3. A method of reducing costs of ethanol production from corn, comprising:
   (a) transforming a corn plant cell with a first nucleic acid molecule expressing a cellulase comprising an exo-1,4-β-glucanase enzyme such that said nucleic acid molecule is incorporated into a nuclear chromosome of said plant cell, said first nucleic acid molecule operably linked to a second nucleic acid molecule directing expression of said enzyme at higher levels in seed cells of said plant than in other cells of said plant, and a third nucleic acid molecule encoding an amino acid sequence directing said enzyme into the secretory pathway, and, optionally, a fourth nucleic acid molecule comprising a nucleotide sequence encoding an endoplasmic reticulum (ER) retention signal, wherein said enzyme is targeted to the cell wall or retained in the ER of said seed cell;

(b) producing from the plant cell a corn plant expressing the cellulase at levels of at least about 1% total soluble protein;

(c) producing a corn crop comprising the corn plant or progeny of the corn plant comprising the first, second, third, and fourth nucleic acid molecules such that at least one of the plants of the crop expresses the cellulase;

(d) harvesting the corn;

(e) producing crop residue from the harvested corn;

(f) contacting the crop residue with the cellulase expressed in the corn plant or the progeny under conditions such that the cellulase degrades cellulose of the crop residue; and (g) producing ethanol by fermentation of the products of degradation of the cellulose of the crop residue.

4. The method of claim 1 wherein expression of said enzyme is directed at higher levels in embryo cells than in other plant seed cells such that the embryo comprises higher levels of said enzyme than in other tissue of said seed.

5. The method of claim 2, wherein said second nucleic acid molecule directs expression of said enzyme at higher levels in embryo cells than in other plant seed cells such that the embryo comprises higher levels of said enzyme than in other tissue of said seed.

6. The method of claim 3, wherein said second nucleic acid molecule directs expression of said enzyme at higher levels in embryo cells than in other plant seed cells such that the embryo comprises higher levels of said enzyme than in other tissue of said seed.

7. A monocotyledonous plant seed having expression of an exo-1,4-β-glucanase enzyme at a level of at least 1% total soluble protein comprising (a) a first nucleic acid molecule encoding said exo-1,4-β-glucanase enzyme, said nucleic acid molecule optimized for expression in a monocotyledonous plant and stably integrated into a nuclear chromosome of said plant;

(b) said first nucleic acid molecule operably linked to a second nucleic acid molecule preferentially directing expression of said enzyme at higher levels in seed cells than in other plant cells;

(c) a third nucleic acid molecule encoding an amino acid sequence directing said enzyme into the secretory pathway of said seed cell; and, optionally, (d) a fourth nucleic acid molecule comprising a nucleotide sequence encoding an endoplasmic reticulum (ER) retention signal, wherein said enzyme is targeted to the cell wall or retained in the ER, such that said plant seed comprises said exo-1,4-β-glucanase enzyme at levels of at least 1% total soluble protein of said seed.

8. The monocotyledonous plant seed of claim 7, wherein said second nucleic acid molecule preferentially directs expression of said enzyme at higher levels in embryo cells than in other plant seed cells such that the embryo of said seed comprises higher levels of said enzyme than in other tissue of said seed.

9. The monocotyledonous plant seed of claim 7, wherein said third nucleic acid molecule encodes an amino acid sequence that secretes said enzyme such that said enzyme is targeted to the cell wall of said seed.

10. The monocotyledonous plant seed of claim 7, wherein said plant comprises said fourth nucleic acid molecule encoding an endoplasmic reticulum retention signal such that said enzyme is retained within the endoplasmic reticulum.

11. The monocotyledonous plant seed of claim 7, wherein said enzyme is targeted to the cell wall.

12. The monocotyledonous plant seed of claim 7, wherein said plant is corn.

13. A plant comprising the seed of claim 7, wherein said seed comprises said first nucleic acid molecule.

14. An embryo of the plant seed of claim 7 wherein said embryo comprises said first nucleic acid molecule.

15. The monocotyledonous plant seed of claim 7, wherein said enzyme expresses at levels of at least 10% total soluble protein.

16. The monocotyledonous plant seed of claim 7, wherein said enzyme expresses at levels of at least 20% total soluble protein.

17. The monocotyledonous plant seed of claim 11, wherein said enzyme expresses at levels of at least 10% total soluble protein.

18. The monocotyledonous plant seed of claim 11, wherein said enzyme expresses at levels of at least 20% total soluble protein.

19. A monocotyledonous plant seed having expression of an exo-1,4-β-glucanase enzyme at a level of at least 0.1% dry weight of seed or 0.1% dry weight of embryo of said seed, comprising (a) a first nucleic acid molecule encoding said exo-1,4-β-glucanase enzyme, said nucleic acid molecule optimized for expression in a monocotyledonous plant and stably integrated into the chromosome of said plant;

(b) said first nucleic acid molecule operably linked to a second nucleic acid molecule preferentially directing expression of said enzyme at higher levels in seed cells than in other plant cells; and (c) a third nucleic acid molecule encoding an amino acid sequence directing said enzyme into the secretory pathway of said seed cell; and, optionally, (d) a fourth nucleic acid molecule comprising a nucleotide sequence encoding an endoplasmic reticulum (ER) retention signal, wherein said enzyme is targeted to the cell wall or retained in the ER, such that said plant seed comprises said exo-1,4-β-glucanase enzyme at levels of at least 0.1% dry weight of said seed or at least 0.1% dry weight of said embryo.

20. The monocotyledonous plant seed of claim 19, wherein said exo-1,4-β-glucanase is expressed at levels of at least 0.1% dry weight of embryo of said seed.

21. The monocotyledonous plant seed of claim 19, wherein said second nucleic acid molecule preferentially directs expression of said enzyme at higher levels in embryo cells than in other plant seed cells such that the embryo of said seed comprises higher levels of said enzyme than in other tissue of said seed.

22. The monocotyledonous plant seed of claim 19, wherein said enzyme is targeted to the cell wall of said seed.

23. The monocotyledonous plant seed of claim 19, wherein said plant comprises said fourth nucleic acid molecule encoding an endoplasmic reticulum retention signal such that said enzyme is retained within the endoplasmic reticulum.

24. The monocotyledonous plant seed of claim 19, wherein said plant is corn.

* * * * *